US011889979B2

(12) United States Patent
Kimpe et al.

(10) Patent No.: US 11,889,979 B2
(45) Date of Patent: Feb. 6, 2024

(54) SYSTEM AND METHOD FOR CAMERA CALIBRATION

(71) Applicants: BARCO NV, Kortrijk (BE); Tom Kimpe, Landegem (BE); Frederik Toune, Bellem (BE); Bart Diricx, Zedelgem (BE); Elie De Brauwer, Wetteren (BE); Albert Xthona, Yamhill, OR (US); Johanna Rousson, Saint Romain de Jalionas (FR); Peter Nollet, Ghent (BE)

(72) Inventors: Tom Kimpe, Landegem (BE); Frederik Toune, Bellem (BE); Bart Diricx, Zedelgem (BE); Elie De Brauwer, Wetteren (BE); Albert Xthona, Yamhill, OR (US); Johanna Rousson, Saint Romain de Jalionas (FR); Peter Nollet, Ghent (BE)

(73) Assignee: BARCO NV, Kortrijk (BE)

( * ) Notice: Subject to any disclaimer, the term of this patent is extended or adjusted under 35 U.S.C. 154(b) by 809 days.

(21) Appl. No.: 16/474,634

(22) PCT Filed: Dec. 30, 2016

(86) PCT No.: PCT/US2016/069521
§ 371 (c)(1),
(2) Date: Jun. 28, 2019

(87) PCT Pub. No.: WO2018/125218
PCT Pub. Date: Jul. 5, 2018

(65) Prior Publication Data
US 2019/0387958 A1 Dec. 26, 2019

(51) Int. Cl.
A61B 1/00 (2006.01)
A61B 5/00 (2006.01)
(Continued)

(52) U.S. Cl.
CPC ...... *A61B 1/00057* (2013.01); *A61B 1/00188* (2013.01); *A61B 5/0077* (2013.01);
(Continued)

(58) Field of Classification Search
CPC ........ A61B 1/00057; A61B 2560/0233; A61B 2562/14
See application file for complete search history.

(56) References Cited

U.S. PATENT DOCUMENTS

| H746 H | * | 2/1990 | Leach | 73/178 R |
| 5,016,173 A | * | 5/1991 | Kenet | A61B 5/0064 382/128 |

(Continued)

FOREIGN PATENT DOCUMENTS

| CN | 101738728 | 6/2010 |
| CN | 102103248 | 6/2011 |
| CN | 105722465 | 6/2016 |

OTHER PUBLICATIONS

European Office Action in corresponding European Application No. 16831876.4, dated May 11, 2020.
(Continued)

*Primary Examiner* — John P Leubecker
*Assistant Examiner* — Jae Woo
(74) *Attorney, Agent, or Firm* — HAMRE, SCHUMANN, MUELLER & LARSON, P.C.

(57) ABSTRACT

A dermatoscope or endoscope inspection device which can be calibrated at high accuracy to be able to focus at a certain depth, e.g. below the top surface of the skin. A calibration pattern is provided or can be located at a reference viewing surface of an inspection device such as a dermatoscope or endoscope. It is important for a dermatoscope to know with the best accuracy available at what absolute depth below the top of the skin the device is focused. The dermatoscope or
(Continued)

endoscope inspection device includes focusing means and by knowing a relationship between a digital driving level which shifts the focus position of the focusing means and the corresponding absolute change in focus depth, it is possible to know how deep the device is focused in absolute terms below the top of the skin.

21 Claims, 11 Drawing Sheets

(51) Int. Cl.
    *G06T 7/00*         (2017.01)
    *H04N 23/50*     (2023.01)

(52) U.S. Cl.
    CPC .... *G06T 7/0012* (2013.01); *A61B 2560/0233* (2013.01); *H04N 23/555* (2023.01)

(56) References Cited

U.S. PATENT DOCUMENTS

| | | | | |
|---|---|---|---|---|
| 5,129,724 | A * | 7/1992 | Brophy | G01B 11/0675 356/511 |
| 5,372,502 | A * | 12/1994 | Massen | A61B 1/24 433/215 |
| 5,424,552 | A * | 6/1995 | Tsuji | G03F 7/70241 250/548 |
| 5,502,311 | A * | 3/1996 | Imai | G03F 9/7026 250/548 |
| 5,604,817 | A * | 2/1997 | Massen | A61C 9/006 348/66 |
| 5,756,981 | A * | 5/1998 | Roustaei | G06K 7/10732 235/462.07 |
| 6,381,013 | B1 * | 4/2002 | Richardson | H01J 37/20 356/392 |
| 6,937,348 | B2 * | 8/2005 | Geng | H04R 25/70 356/610 |
| 7,057,737 | B2 * | 6/2006 | Millerd | G01J 9/02 356/495 |
| 7,385,708 | B2 * | 6/2008 | Ackerman | H04N 13/254 356/603 |
| 7,625,335 | B2 * | 12/2009 | Deichmann | G01B 11/24 600/117 |
| 7,642,506 | B2 * | 1/2010 | Wang | A61B 6/583 378/207 |
| 7,751,871 | B2 * | 7/2010 | Rubbert | A61B 5/0088 600/407 |
| 8,304,704 | B2 * | 11/2012 | Hing | G02B 21/241 250/201.3 |
| 8,462,357 | B2 * | 6/2013 | Rodrigue | G01B 11/245 356/601 |
| 8,644,912 | B2 * | 2/2014 | Bambot | G01N 21/6486 600/478 |
| 9,220,412 | B2 * | 12/2015 | Cuccia | A61B 5/0059 |
| 9,444,981 | B2 * | 9/2016 | Bellis | H04N 5/2251 |
| 9,486,284 | B2 * | 11/2016 | Depfenhart | A61B 18/203 |
| 9,786,053 | B2 * | 10/2017 | Zweig | G06T 7/80 |
| 10,984,213 | B2 * | 4/2021 | He | G09G 3/3208 |
| 11,116,383 | B2 * | 9/2021 | Nir | G06T 15/205 |
| 2001/0051761 | A1 * | 12/2001 | Khadem | A61B 34/20 600/117 |
| 2002/0016539 | A1 * | 2/2002 | Michaelis | A61B 5/7264 600/407 |
| 2003/0088179 | A1 * | 5/2003 | Seeley | A61B 6/487 600/424 |
| 2003/0164952 | A1 * | 9/2003 | Deichmann | G01B 11/24 356/603 |
| 2004/0092802 | A1 * | 5/2004 | Cane | A61B 5/0059 600/306 |
| 2004/0252195 | A1 * | 12/2004 | Lu | G02B 7/02 348/188 |
| 2005/0088435 | A1 * | 4/2005 | Geng | H04R 25/658 345/419 |
| 2005/0178976 | A1 * | 8/2005 | Steele | G02B 21/26 250/440.11 |
| 2005/0275849 | A1 * | 12/2005 | Freimann | G01B 9/02039 356/521 |
| 2006/0122515 | A1 * | 6/2006 | Zeman | H04N 5/2354 600/473 |
| 2007/0024946 | A1 * | 2/2007 | Panasyuk | A61B 5/416 359/253 |
| 2007/0142707 | A1 * | 6/2007 | Wiklof | A61B 1/00057 600/117 |
| 2007/0161854 | A1 * | 7/2007 | Alamaro | A61B 5/1076 600/109 |
| 2007/0173792 | A1 * | 7/2007 | Arnoldussen | A61F 9/00804 606/4 |
| 2008/0012850 | A1 * | 1/2008 | Keating, III | H04N 13/254 348/E13.016 |
| 2008/0297911 | A1 * | 12/2008 | Christenson | B29D 11/00028 359/666 |
| 2009/0138234 | A1 * | 5/2009 | Sundman | A61B 5/0064 702/167 |
| 2009/0173889 | A1 * | 7/2009 | Costantino | G01N 21/6458 250/252.1 |
| 2010/0020180 | A1 * | 1/2010 | Hill | H04N 5/3415 348/188 |
| 2010/0040355 | A1 * | 2/2010 | Craen | A61B 1/0019 396/90 |
| 2010/0108873 | A1 * | 5/2010 | Schwertner | G06T 7/55 250/206 |
| 2010/0114264 | A1 * | 5/2010 | Lechthaler | A61N 5/0616 607/88 |
| 2010/0114266 | A1 * | 5/2010 | Lechthaler | A61N 5/0616 607/94 |
| 2010/0121201 | A1 * | 5/2010 | Papaioannou | A61B 5/0064 382/128 |
| 2010/0161266 | A1 * | 6/2010 | Meijles | G01N 21/93 702/94 |
| 2011/0017902 | A1 * | 1/2011 | Hing | G02B 21/241 250/201.2 |
| 2011/0054252 | A1 * | 3/2011 | Ozaki | A61B 1/00089 600/109 |
| 2011/0069162 | A1 * | 3/2011 | Ozawa | A61B 1/0008 348/E7.085 |
| 2011/0096981 | A1 * | 4/2011 | Arnison | G03F 9/7026 382/151 |
| 2011/0124988 | A1 * | 5/2011 | Cuccia | A61B 5/0059 600/310 |
| 2011/0148764 | A1 * | 6/2011 | Gao | G06F 3/0317 250/252.1 |
| 2011/0304849 | A1 * | 12/2011 | Chi | G01N 21/6452 356/243.1 |
| 2012/0092461 | A1 * | 4/2012 | Fisker | A61B 5/1077 348/46 |
| 2012/0169885 | A1 * | 7/2012 | Wang | G03B 43/00 348/E17.002 |
| 2012/0172685 | A1 * | 7/2012 | Gilbert | A61B 5/0077 600/306 |
| 2012/0268800 | A1 * | 10/2012 | Tsai | H04N 1/3876 358/448 |
| 2013/0002832 | A1 * | 1/2013 | Lasenby | G01B 11/16 348/51 |
| 2013/0027515 | A1 * | 1/2013 | Vinther | A61B 1/227 348/E13.02 |
| 2013/0258044 | A1 * | 10/2013 | Betts-Lacroix | H04N 13/243 348/E5.09 |
| 2013/0321585 | A1 * | 12/2013 | Hassebrook | G06K 9/00 348/46 |
| 2014/0022356 | A1 * | 1/2014 | Fisker | A61B 5/1079 348/47 |
| 2014/0041242 | A1 * | 2/2014 | Engel | G01B 11/03 33/502 |
| 2014/0111621 | A1 * | 4/2014 | Sneyders | G01B 11/2545 348/46 |
| 2014/0171759 | A1 * | 6/2014 | White | A61B 5/6835 600/306 |
| 2014/0184881 | A1 * | 7/2014 | McKinley | H04N 5/2257 348/345 |

(56) References Cited

U.S. PATENT DOCUMENTS

| | | | | |
|---|---|---|---|---|
| 2014/0336461 | A1* | 11/2014 | Reiter | A61B 1/00009 600/111 |
| 2015/0018645 | A1* | 1/2015 | Farkas | A61B 90/94 600/317 |
| 2015/0054922 | A1* | 2/2015 | Fisker | G01B 11/2513 348/46 |
| 2015/0091447 | A1 | 4/2015 | Kubo | |
| 2015/0146214 | A1* | 5/2015 | Naoi | G01M 11/0264 356/521 |
| 2015/0201117 | A1* | 7/2015 | Acher | H04N 5/2354 348/79 |
| 2015/0320316 | A1* | 11/2015 | Dhawan | A61B 5/445 600/473 |
| 2015/0347833 | A1* | 12/2015 | Robinson | G06K 9/00536 348/49 |
| 2015/0374233 | A1* | 12/2015 | Zhang | A61B 3/12 351/246 |
| 2016/0058288 | A1* | 3/2016 | DeBernardis | A61B 5/0075 600/477 |
| 2016/0061654 | A1* | 3/2016 | Corwin | G01N 21/274 702/104 |
| 2016/0122723 | A1 | 5/2016 | Retting et al. | |
| 2016/0143509 | A1* | 5/2016 | Olds | A61B 1/00009 600/111 |
| 2016/0282598 | A1 | 9/2016 | Besley et al. | |
| 2016/0287141 | A1* | 10/2016 | Sidlesky | G02B 23/2415 |
| 2016/0334332 | A1* | 11/2016 | Magnussen | G01N 21/474 |
| 2017/0352161 | A1* | 12/2017 | Ganapati | H04N 13/254 |
| 2018/0007346 | A1* | 1/2018 | Ushijima | G02B 23/24 |
| 2018/0046875 | A1* | 2/2018 | Caluser | A61B 5/0077 |
| 2018/0068466 | A1* | 3/2018 | Bronkalla | A61B 6/585 |
| 2018/0186082 | A1* | 7/2018 | Randhawa | B33Y 30/00 |
| 2018/0231475 | A1* | 8/2018 | Brown | A61B 5/05 |
| 2019/0137340 | A1* | 5/2019 | Ogino | G01J 3/0297 |
| 2019/0142257 | A1* | 5/2019 | Vinther | A61B 1/227 600/200 |
| 2019/0247132 | A1* | 8/2019 | Harks | G06T 7/30 |
| 2019/0254529 | A1* | 8/2019 | Pesach | A61B 5/0088 |
| 2020/0017406 | A1* | 1/2020 | Wilson | G06F 1/1605 |
| 2020/0318957 | A1* | 10/2020 | Boarino | G01B 21/042 |
| 2020/0359890 | A1* | 11/2020 | Zhang | G16H 50/20 |
| 2021/0068655 | A1* | 3/2021 | Zhang | A61B 3/103 |
| 2021/0169320 | A1* | 6/2021 | Tripathi | A61F 9/00736 |
| 2021/0259570 | A1* | 8/2021 | Brisby | A61B 5/4869 |
| 2021/0330278 | A1* | 10/2021 | Fukutsuka | A61B 7/04 |
| 2021/0386277 | A1* | 12/2021 | Gordon | A61B 1/00096 |

OTHER PUBLICATIONS

Chinese Office Action in corresponding Chinese application 201680092128.2 dated Sep. 29, 2021.
European Office Action in corresponding European Application No. 16831876.4, dated Jan. 29, 2021.
International Search Report in corresponding PCT/US2016/069521, dated Sep. 27, 2017.
Written Opinion in corresponding PCT/US2016/069521, dated Sep. 27, 2017.
International Preliminary Report on Patentability in corresponding PCT/US2016/069521, dated Mar. 20, 2019.
Second Written Opinion in corresponding PCT/US2016/069521, dated Nov. 30, 2018.
Silvio Savarese et al., 3D Reconstruction by Shadow Carving: Theory and Practical Evaluation, International Journal of Computer Vision 71(3), 305-336, 2007.
Silvio Savarese et al., Shape Reconstruction from Shadows and Reflections, California Institute of Technology, 2005, pp. 1-141.
Office Action issued in corresponding Chinese Application No. 201680092128.2, dated Apr. 22, 2022, with English translation.
Examination Report issued in Australian Application No. 2016433859, dated Sep. 5, 2022.

* cited by examiner

SYSTEM AND METHOD FOR CAMERA CALIBRATION

FIELD OF THE INVENTION

The invention relates to the field of diagnostic imaging, and to an inspection device and how to calibrate a camera of an inspection device for diagnostic imaging.

BACKGROUND OF THE INVENTION

A dermatoscope can be used for diagnostic imaging of skin. Today most dermatoscopes are still anologue devices, meaning they comprise a magnifying glass with lighting around it. Dermatoscopes do not only look at the top surface of the skin, but they image at different depths in the skin, down to about 3 mm or more. The dermatologist can adjust the focus such that the focal point is set to a "desired depth", and this is decided by the dermatologist based on experience. As the focus is changed, specific skin structures will come into focus and other ones will go out of focus. The expert dermatologist recognizes these structures and knows continuously where he/she is when browsing the skin (e.g. at the top, the epidermis, the dermis, . . . ). For non-experts, however, this is very difficult and most often non-experts don't know exactly at what depth the device is focused.

The diagnosis of certain types of skin cancer is not easy and analogue devices do not record the images seen by the doctor when making the diagnosis. This results in a conservative approach of making more biopsies than would be required if a better method of diagnosis were available.

FIG. 1 shows a schematic representation of different skin layers on the y axis, and the penetration depth (in mm) for light of different wavelengths (in nm) on the x axis. In fact, the longer the wavelength, the deeper it penetrates into the skin tissue and the deeper is the focus corresponding to a certain wavelength. In each layer, there are characteristic structures present, thus there will be "sharp" structures visible from the surface and down to more than 3 mm depth. Thus, conventional autofocus algorithms, e.g. such used in smartphones, will not work since such algorithms rely on the image being sharp once the focal point is set correctly.

Recently digital dermatoscopes have been introduced. These devices are the digital equivalent of the regular analogue dermatoscope. Today, digital dermatoscopes offer mostly the same functionality as analogue dermatoscopes; but they can take an image of the skin and the dermatologist can (manually) control the focus depth.

With the emergence of digital dermatoscopes it becomes possible to decouple the "imaging" of a skin lesion from the "reading/diagnosing" of it. General Practitioners (GP's) or nurses could e.g. image skin lesions and send the images to dermatologists for diagnosis.

However, this requires that images are acquired at the correct focus depth (or rather at a multitude of correct focus depths) and that it is known which focus depth is associated with which image.

Moreover, it is crucial to know with a very high accuracy the depth of the lesion. In fact, in the case of melanoma for example, the depth of the lesion provides an estimate of the chances of survival of the patient after 5 years. The depth of the melanoma is one of the most crucial parameters to estimate in order to obtain an accurate diagnosis. Therefore, the focus depth needs to be perfectly controlled throughout the lifetime of the device.

US20160282598A1 (Canon 3D) discloses how to calibrate a microscope for doing e.g. 3D analysis, by using a calibration target with a test pattern. The calibration target is physically positioned on a movable stage below the optical system.

US20160058288A1 (Mela, dermatoscope) discloses three-dimensional imaging of tissue, using "the known camera calibration of the system" as calibration reference.

SUMMARY OF THE INVENTION

With respect to inspection devices for medical applications such as dermatological inspection devices or endoscopes there is a need to:
- Provide a method for automatically controlling focus depth when imaging targets that have structures throughout its volume, since automatic focus algorithms as they exist today are not suitable.
- Be able to associate digital driving values that control focus to an absolute value of the focus depth, and to associate a range of digital driving values that control focus to a range of absolute values of the focus depth.
- Linking acquired images to specific absolute focus depth values.

In an aspect, the present invention provides methods to calibrate at high accuracy the focus position at the top surface of the skin. For this reason, in a preferred embodiment, a calibration pattern is provided or can be located at a reference viewing surface of an inspection device such as a dermatoscope or endoscope. The reference viewing surface can be on the lower surface of the front glass of the inspection device, which during use is in contact with the skin of a patient or is inserted into a body cavity at the end of an endoscope. It is also advantageous for a dermatoscope to know with the best accuracy available at what absolute depth below the top of the skin the device is focused. This can be achieved by embodiments of the present invention by providing focusing means and by knowing a relationship between a digital driving level which shifts the focus position of the focusing means and the corresponding absolute change in focus depth. From this it is possible to know how deep the device is focused in absolute terms below the top of the skin.

Similar considerations apply to an endoscope.

More than one calibration patterns can be used. By using two patterns at different depths where the difference in depth between these two patterns is known, the relationship between difference in depth and driving levels of the focusing means can be established by focusing on these two patterns and determining the corresponding difference in digital driving value that shifts the focus position. The relationship between the absolute difference in focus depth and the corresponding change in digital driving value is then established. Such a relationship is a calibration.

To allow repeated calibration a reference distance is required that does not change over the lifetime of the inspection device. Embodiments of the present invention select this distance to be a known fixed depth relationship between the calibration pattern and the front side of the glass which during inspection will be applied directly to the skin of a patient.

An advantage for locating the calibration pattern at a known distance to the front glass reference viewing surface is that it allows autofocusing. A typical existing auto focus algorithm changes focus iteratively up to the point where maximum sharpness of the image is obtained. It is assumed that the focus is then set correctly. This works with natural scenes (photographs) where the picture is not sharp when the focus is wrong.

But this does not work in with diagnostic images of the skin as the skin contains well defined structures at different depths. Therefore, changing the focus results in several depths where sharpness is obtained. And moreover, if autofocus were to be performed, the depth at which the focus is obtained would not be a reliable value.

Providing a calibration a pattern on the front glass reference viewing surface, which is preferably the surface to be in contact with the skin, means that the focus is therefore on the top of the skin and not within it since the glass is pressed on the skin.

Embodiments of the present invention may make use of extensions to the viewing end of the inspection device. In such a case the reference viewing surface is that surface which comes in contact with the skin which may not be front glass. The extensions can be tips of different lengths. Thus, a main goal for calibration can be to be able to focus on the end of the extension, and more precisely the surface to be in contact with the skin.

A further problem with focusing devices using a mechanical system to change focus having moving parts is backlash. Backlash can result in different focus positions depending upon the direction of travel of the focusing device. There are known methods of avoiding backlash but they can increase the bulk of the inspection unit. Embodiments of present device avoid backlash by the use of deformable lenses.

In one aspect of the invention calibrated inspection unit is provided for direct application to the skin of a patient or for examining the interior of a hollow organ or cavity of the body of a patient, said calibrated inspection unit comprising an optical array of elements in an optical path comprising:
at least one light source,
an image capturing device having a field of view,
an imaging lens having a radius of curvature and a focal length defining a position of a focus point along the optical path,
focusing means for changing the focus position along the optical path as a function of adjustment values, and
a reference viewing surface through which images are captured for the image capturing device, characterized by
a calibration pattern for locating in a fixed position with respect to the reference viewing surface and in the field of view of the image capturing device, and
a calibration means for defining a relationship between first adjustment values of the focusing means and the positions of focus points along the optical path, including a second adjustment value for a focus position at the fixed position of the calibration pattern.

The calibration means can be a relationship that is pre-calculated and stored or the calibration means can generate the relationship at any time, e.g. starting from the stored second adjustment value being for example the digital value corresponding to a reference position. Then a "distance step per change in digital drive" can be determined to complete the calibration.

The calibration pattern can not only be used for focus calibration, but can also be used for absolute color calibration. A single calibration pattern can be used or a combination of multiple calibration patterns, the calibration patterns having different functions. Accordingly, the calibration pattern can comprise a color calibration chart. The color calibration chart can be used for absolute color calibration. This has the advantage that it is possible to include absolute color calibration and correct possible drift of the light sources.

The present invention provides means suitable for referring to an absolute reference point of calibration of an image capturing device. And when the unit is investigating objects having a multiple of possible focus points at different depths, the unit can be instructed to focus the light at a required absolute depth.

The calibration using the calibration pattern or patterns can also provide a means of correcting a predefined or pre-calibrated relationship of a focus position along the optical path as a function of adjustment values at a later date, e.g. by the practicing doctor.

The at least one light source can be centred on a first wavelength and have a first spectral bandwidth.

This makes it possible to work with light of a certain colour or wavelength range, having desired properties, for example penetration depth into skin which is wavelength dependent.

The at least one light source may comprise a plurality of light sources, each light source being centred on a different wavelength and having a spectral bandwidth, and the first adjustment values of the focusing means and the positions of the focus points along the optical path can be different for each wavelength.

This makes it possible to have the inspection unit operating with combinations of several colours or wavelength bands and hence combine their properties. Additionally, the light sources can be independently controlled, which enables a customized calibration and operation.

There can be a second calibration pattern provided for locating in a second fixed known position with respect to said reference position and in the field of view of the image capturing device, and a stored third adjustment value for a second focus position at the second fixed known position of the second calibration pattern. This makes it possible to relate to a second absolute focus point which can be located at a known position from the first focus point, so that adjustment values can be related to an absolute depth. Additionally, two or more calibration patterns can provide an estimate of a step size along the optical axis of the optical path related to a change of an adjustment value. The relationship between a focus position along the optical axis and the adjustment values might shift due to aging. With two or more patterns at different depths, it is possible to identify and hence to correct for such a drift.

In addition there can be further calibration patterns ate points located between positions of the first and second calibration pattern. This can provide higher calibration accuracy. An example is first and second calibration patterns on each side of the front glass with extra calibration patterns embedded in the glass at intermediate positions.

Accordingly, there can be a front plate provided in the exit pupil of the optical array, and wherein the calibration pattern can be provided on at least one of the two surfaces of the front plate and/or inside the front plate.

Thus, the calibration pattern may be place on, or inside, the front glass of the inspection unit.

In another aspect of the invention, the calibration pattern can be placed on the skin of a patient as a tattoo or a stamp. This makes it possible to have calibration points on the actual object to be investigated.

A calibration pattern can be placed on a substrate being thinner than the front glass, which is positioned on top of the front glass or inside the housing, or the calibration pattern is put directly on a part of the housing.

Alternatively, the calibration pattern can be put on a substrate or film that can be added between the front glass and the object to be investigated, e.g. the skin. Alternatively, the substrate with a pattern can be put inside the housing of the inspection unit. Alternatively, the calibration pattern can be put directly onto a part of the housing. In all cases the substrate with pattern is put within the field of view of the imaging device.

In another aspect of the invention, the focusing means can be provided by any of: The imaging lens which is a liquid lens or the image capturing device which can be configured to be translated along the optical axis, or the imaging lens which can be configured to be translated along the optical axis. Additionally, the first and second adjustment values the above configurations can be driving voltages. When the imaging lens is a liquid lens, the focal length of the lens in an additional piece keeps the camera lens operating in a range with high sensitivity.

Thus, the inspection unit may be implemented by using a high precision liquid lens, and/or a moving sensor, and/or a moving lens, for which the focus position along the optical axis can be adjusted by changing a driving voltage.

In another aspect of the invention the focusing means can comprise means for calculating the modulation transfer function of the optical array.

This makes it possible to obtain information on for example the resolution of the camera.

In another aspect of the invention, the calibration pattern can be a three-dimensional pattern defining a plurality of fixed known positions from the reference position when said three-dimensional pattern is installed on the inspection device at the fixed distance to the reference viewing surface. The focusing means further can have a plurality of adjustment values for focus positions at a plurality of fixed known positions of the three-dimensional calibration pattern, e.g. when translated in the x, y plane, whereby the calibration patterns are made in such a way that the position in the x, y plane can be accurately determined. Additionally, a three-dimensional calibration pattern can be engraved, etched, milled or printed within a calibration substrate. Additionally, the calibration pattern can comprise parallel lines which are in a plane which form an angle with the plane of the image acquisition device. Additionally, the calibration pattern can comprise a pattern which is in a plane parallel to the plane of the sensor. Additionally, the distances between patterns can be correlated to their distance from the surface of the substrate.

This aspect of the invention makes it possible to calibrate towards absolute points outside or beyond the inspection unit. The calibration pattern can be a phantom of human skin, which could be used to check the accuracy of the calibration. The calibration pattern can also be formed by part of the housing of the unit, e.g. edges of the housing could detected by edge detecting methods.

In another aspect of the invention, the calibrated inspection unit can be configured to operate with a second piece providing a second exit pupil. Additionally, a second front glass is provided at the second exit pupil and at least one calibration pattern is provided at a known distance from the second front glass. Additionally, the second piece can comprise a lens whose focal length relates to the length of the piece. Additionally, the imaging lens can be a liquid lens and the focal length of the lens in the additional piece keeps the camera lens operating in a range with high sensitivity, for example a small focal depth step size.

This makes it possible to provide a shape of the housing of the inspection unit that has a better suitable geometry, for example, a more elongated narrow shape that can reach the skin in narrow regions like between fingers. If e.g. a liquid lens is used it is desirable to keep it working in its most sensitive range where fine tuning is possible. An additional lens in the second piece can alter the focus length to better suit the liquid lens. Hence when the imaging lens is a liquid lens, the focal length of the lens in an additional piece keeps the camera lens operating in a range with high sensitivity.

In another aspect of the invention, there can be calibration information put in optical codes such as a barcodes or QR (Quick Response) codes next to the calibration pattern.

The optical code such as a barcode or QR code can store relevant information on the calibration pattern and/or information related to the user, for example a customized calibration procedure.

A means can be provided to detect if the front surface is in contact with an external object, such as the skin, e.g. by use of a touch screen in the front surface. This could be used to known when absolute focus setting is preferred and when an auto focus algorithm is preferred.

DETAILED DESCRIPTION OF THE INVENTION

Figure 1:
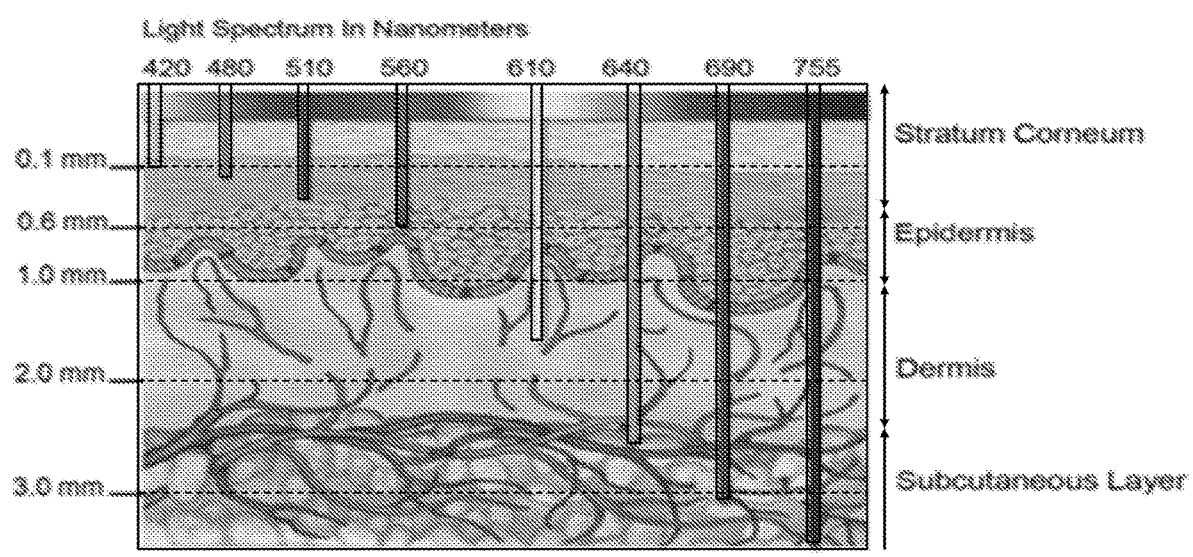
FIG. 1 shows penetration depths in the skin for different wavelengths.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The present invention relates to optical systems with variable optical focus and relate to solving the problem of variability in characteristics. Focus in such a system can be controlled by means of digital values or driving levels. These digital values are applied to an actuator which can either mechanically change the position of a lens or lenses to change the focus, or in the case of a liquid lens (for example from Varioptic®) applies voltage to change the curvature of a liquid lens and therefore the focus. The relationship between these digital values and the exact focus depth can suffer from variability, e.g. caused by mechanical tolerances, liquid lenses being sensitive to temperature effects, . . . . Embodiments of the present invention make sure that a digital drive value will always be associated with a specific focus depth. Also the optical system of an inspection device according to embodiments of the present invention can be calibrated at manufacturing, and corrections can be made later to correct for the accuracy of the focusing system being influenced by temperature changes which could change the focus depth. In critical applications such as dermatology these changes in focus depth can be of the same magnitude or even larger than the accuracy required in focusing (e.g. 100-120 µm) the instrument for an accurate diagnosis.

Figure 17:
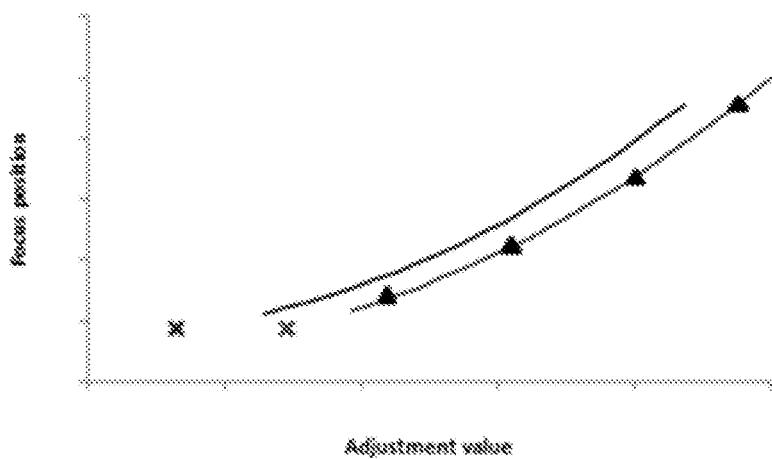
FIG. 17 shows how calibration curves representing different drive levels for focus positions can change with time due to various environmental effects.

In accordance with embodiments of the present invention adjustment values for focusing means which correspond to a given focus position along the optical axis, the right hand cross in FIG. 17 combined with focus positions along the optical axis as a function of adjustment values as shown in the lower solid line compensation or correct can be used (using a pre-determined potentially non-linear transformation) of the focus position along the optical axis as a function of adjustment values as can be seen from the upper solid line.

This can be done with only one calibration point being remeasured when the reference adjustment value corresponding to the given focus position along the optical axis changes (cross on the left), due to for example aging, environmental conditions, mechanical change (due to shock, vibration . . . ).

Figure 2:
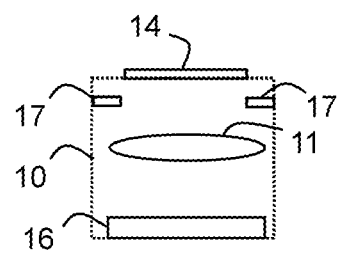
FIG. 2 shows the fundamental parts of a dermatoscope.

FIG. 2 illustrates a basic configuration of a digital dermatoscope according to embodiments of the present invention. It comprises a housing 10 (of arbitrary shape), an image capturing device such as a camera sensor 16, a camera lens 11, and a front glass 14 which forms a reference viewing surface. At least one light source is provided, or a plurality of light sources 17 are provided, but the dermatoscope can in principle function with ambient light. The lens can for example be a variable focus liquid lens such as the "Caspian S-25H0-096" from Varioptic®. The sensor board can for example be "LI-IMX274-MIPI-M12" from Leopard Imaging Inc. Internal light sources can be implemented with for example the Luxeon® C or Z LED series from Lumileds®.

It is important to note that although the term front glass is used throughout the application, it does not need to be glass, it can be any transparent substrate, for example a transparent plastic substrate, etc. Also means can be provided to detect when the viewing surface touches the skin, the viewing surface can be a touch screen.

Figure 11:
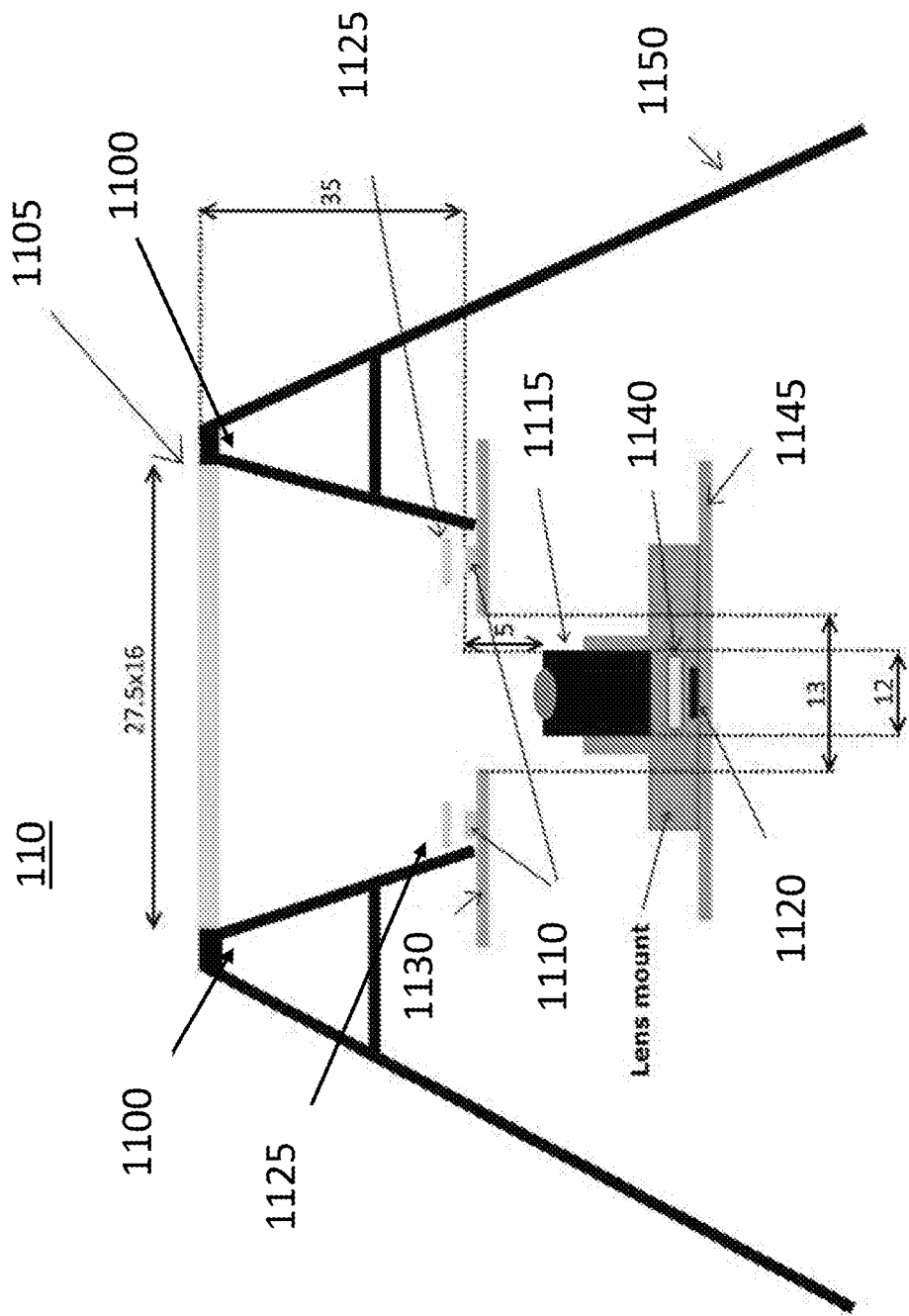
FIG. 11 shows a schematic side view of a dermatoscope according to embodiments of the present invention.

FIG. 11 shows a schematic side view of a dermatoscope 110 according to embodiments of the present invention. Embodiments of the present invention may also be used at the end of an endoscope.

The dermatoscope 110 comprises advantageously a plurality of light sources 1110 having different spectral bands, wherein the focus associated to each spectral band is at a different depth in human or animal skin, as shown on FIG. 1. Thus, the dermatoscope 110 uses multispectral imaging. The dermatoscope 110 sequentially (or in embodiments of the present invention simultaneously) illuminates a region of interest of the skin with light sources of different spectral bands. Each time an image is acquired a multispectral scan is made.

In an embodiment of the present invention, the light sources can be LEDs light sources.

The dermatoscope 110 further comprises an image acquisition device 1120, which can be a CCD or a camera sensor, CMOS sensor or a line scanner. Thus, the term "sensor" refers to any suitable image acquisition device 1120.

The image acquisition device, e.g. sensor used in an embodiment of the present invention provides a resolution at the surface of the skin of about 6.6 µm. The field of view of the device shown on FIG. 11 is 27.5×16 mm, at the surface of the skin. At deeper depths, the field of view is slightly increased. The field of view of the device is preferably selected so that it can view common types of skin defects, lesions etc.

The spectral sensitivity of the image acquisition device, e.g. sensor has to match the spectral bandwidth of the light sources. Greyscale sensors can be used for the present application, however, although color sensors may also be used for the present invention.

Figure 12:
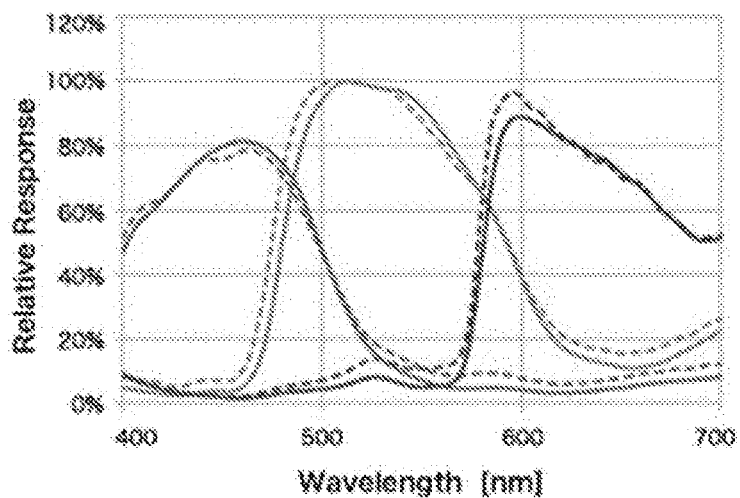
FIG. 12 shows the spectral sensitivity of a sensor according to the present invention.

The spectral sensitivity of a Sony sensor which can be used with embodiments of the present invention is shown on FIG. 12. The solid line shows the Sony IMX214 and the dashed line shows the Sony IMX135.

In an example of an embodiment of the present invention, a plurality of light sources such as LEDs are arranged in two arrays, i.e. LED arrays, each array, i.e.LED array comprising seven light sources, e.g. LEDs.

In a preferred embodiment of the present invention, the light sources are arranged in a ring. Two light sources of the same type (i.e. color and optionally polarization) can be placed on the opposite side of the ring from each other. In an embodiment according to the present invention, seven different types of light sources, e.g. LED light sources having different spectral bands are arranged in a ring.

The following spectral bands can be selected:
1. White unpolarized
2. Blue unpolarized
3. White polarized
4. Blue polarized
5. Green polarized
6. Deep red polarized
7. Far red polarized To generate polarized light, a polarizer 1125 may be inserted in the device as shown on FIG. 11.

Further, a cross polarizer 1140 (the combination of the two polarizers which are crossed with respect to each other) can be used in front of the sensor 1120 of the image acquisition device. Such a cross polarizer can filter out parasitic reflections due to light scattering. The image acquisition device is further provided on a PCB sensor board 1145.

An LED PCB board 1130 is provided in a vicinity of the LED array 1110 as shown on FIG. 11.

Optionally, a fastening means such as magnets can be placed near the front edges of the housing (in a proximity of the front plate) which can be used to fix a cone extension piece, described below.

All these components are arranged in a housing 1150. The housing can be cone shaped, or rectangular, cylindrical, etc.

Figure 13:
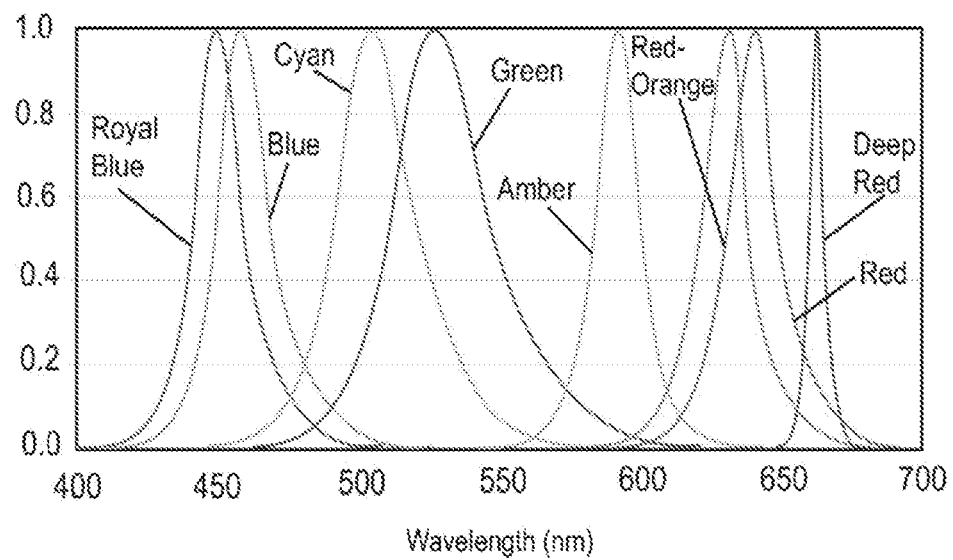
FIG. 13 shows the normalized spectral power distributions of light sources used with embodiments of the present invention.
Figure 16:
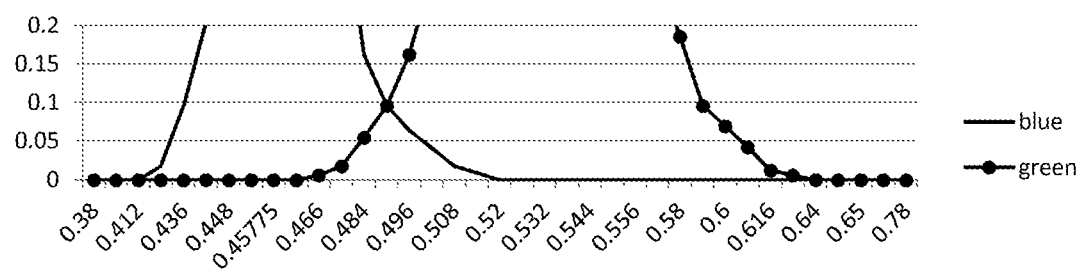
FIG. 16 shows a close up of FIG. 13 in the region of the overlap between blue and green light sources.

FIG. 13 shows the normalized spectral power distributions of LED light sources used with embodiments of the present invention. The LEDs may be acquired from the supplier "Lumiled" and the series is called "Luxeon Z" for blue, green, deep red and white, and "Luxeon C" for far red. Different LED's are used for the different colors. FIG. 16 shows a close up of FIG. 13 in the region of the overlap between the blue and green light sources.

In the example shown on FIG. 11, the optical centre of each LED 1110 is positioned on a circle having a radius of 7.5 mm, in exception to the far-red polarized LED for which the circle has a radius of 7.9 mm.

The centre of the LED ring corresponds to the image acquisition device optical axis and has an opening for the lens, for example a liquid lens. The radius of the opening can be 5 to 15 6.5 mm for example.

The front glass 1105 of the device of the present invention can comprise an anti-reflection coating on the front glass, provided on one or both sides of the front glass. This coating preferably provides as little filtering as possible, and no other filters need to be used. The front glass has an upper surface which is inside the device and a lower surface which, during use, can be in direct contact with the skin of a patient. The thickness of the front glass is preferably in the range of 1 to 2 mm.

In order to calibrate the focus position, digital driving levels of focusing means are determined to generate a calibration, depending on the type of dermatoscope used. In some embodiments, the focusing means can be provided by the image acquisition device which can be translated along the optical axis of the optical path, and therefore its position with respect to the focus point needs to be calibrated. In other embodiments, the focusing means can be provided by changing the position of an imaging lens, the imaging lens being able to move along the optical axis of the optical path. In other embodiments, the focusing means can be provided by a liquid lens wherein it is the change in curvature of the -liquid lens which can be modified, for example a lens from Varioptic®, wherein the voltage changes the curvature of a liquid lens and therefore the focus position. In all these embodiments, the focus is controlled by means of digital values or driving levels. When the imaging lens is a liquid lens, the focal length of the lens in an additional piece keeps the camera lens operating in a range with high sensitivity.

The device shown on FIG. 11 comprises a liquid lens 1115 whose distance to the front glass is 40 mm. This distance is calculated so that the liquid lens is in the flat position, and thus the optical system has limited aberrations and distortions and has the smallest focus depth size, and provides the best optical performance. The precision of the focus depth of the optical system with the liquid lens is of approximately 120 μm.

The focus depth as a function of the digital driving value for the focusing means is often not linear throughout the entire range of movement of the moving part of the focusing means at a given wavelength. Therefore, the present invention provides different types of calibrations: a local and quick calibration which can be calibrated iteratively each time by evaluating the sharpness and changing the focus so that a sharpness metric is maximized, a broad calibration which spans a broader range of focus positions along the optical path, and which allows to detect if the focusing means is outside of a linear range.

The accuracy of both types of calibrations is of the same order. The broad calibration can be performed using an additional substrate, which enables determination of the relationship between the digital driving level and the focus on the pattern in the field of view, of which the focus depth is known. For a further focus positions the focusing means is used to determine the digital driving levels for different focus depths. This can be done using a calibration target which has patterns at different focus depths. During this broad calibration, the relationship between the focus depth for the fixed pattern and a range of focus depths corresponding to depths deeper in the skin, i.e. beyond the front of the device is established. This type of calibration can be performed in the factory but also later, by a technician on site, for example or can be implemented within a docking station, while charging the device.

The local and quick calibration performs the first part of the broad calibration, but is used to take into account the external conditions of operation of the image acquisition, and thus takes into account the temperature, etc. Based on this self-calibration, the calibration using an external object is corrected. This way the relationship of the digital driving levels to focus positions at different depths is known more accurately, even with the absence of the external calibration target (broad calibration).

The range of the broad calibration can be optionally limited to the first millimeters of focus distance, in order to capture skin lesions. Although the optical system is capable of going above this range, the absolute focus depth is calibrated in this range where a skin lesion is likely to occur. For an endoscope a larger range can be used.

This broad calibration can be performed in the factory but in order to ensure the reliability of the device throughout its lifetime it is preferable to provide means for performing this broad calibration whenever required, for example during charging of the device (within a docking station for example). The linear calibration may advantageously be performed quickly, each image acquisition, or at device start-up to compensate for minor deviations.

The local calibration is first described as a first embodiment and second embodiment. The broad calibration is described as a third embodiment of the present invention. Note that the broad calibration may not be required for every type of device. Some devices according to the present invention show a linear range over the entire range of the moving part, and thus such a calibration may not be required.

In the first embodiment according to the present invention, in order to calibrate the focusing means by controlling the position of the focus at a given wavelength, a calibration pattern may be positioned at a known position along the optical axis of the image acquisition device, e.g. sensor and within its field of view. The pattern can for example be placed at the edge of the FOV so as not to disturb the images. The images presented to the users may even not comprise the image of the calibration pattern so as not to disturb the user, but only the central part, comprising the object of interest.

As the focus position or focal length can depend on the wavelength, each light source, having a different spectral bandwidth centered on a different wavelength will in this case have different focus positions for a same configuration of the device (same curvature of the liquid lens or same position of the image acquisition device), or a different configuration for a same focus position. Thus, the following calibrations are preferably performed for each wavelength. However, the calibration can also be performed at one wavelength, for instance the shortest wavelength, and then the calibration extrapolated to all the other wavelengths of the device, by means of a formula, a look up table, an algorithm, etc.

As the calibration can be wavelength dependent, and the light sources have a narrow spectral bandwidth, the chromatic aberrations associated to each light source can be negligible. As the calibration measurements are performed separately for each wavelength, chromatic aberrations are corrected for each wavelength.

An inspection device according to the present invention can be used to analyze an object of interest at the skin surface and below the skin surface. Calibration, is used to be able to know at which depth the measurement is being performed. As there can be medically relevant information in an entire volume of skin, the inspection device according to embodiments of the present invention can map structures at different depths accurately. This first embodiment aims at calibrating the device at a known fixed distance from the image acquisition device, above or at the level of the skin surface with a known calibration pattern, thus record the driving level for which the device is focused in said known fixed position at one of the wavelengths.

For example, a calibration pattern can be placed directly onto one or both of the upper and/or lower surface of the front glass 14. Such calibration pattern is at a fixed position with respect to a reference viewing surface of the device. In this case the viewing surface is the lower surface of the front glass 14. This can be used to calibrate the image acquisition device, e.g. camera in absolute measures and provide a reference point to determine the focus depth. By putting the calibration pattern onto the glass, no additional parts have to be added and/or correctly positioned, when performing the calibration. This embodiment provides a fixed distance between the calibration pattern and the image acquisition device, e.g. camera sensor (or between the calibration pattern and the magnifying lens, in case of using a moving image acquisition device, e.g. sensor).

The advantage of providing a calibration pattern on the lower surface as reference viewing surface which is to be placed in contact with the skin in use is that the device is then calibrated for the skin surface. Additionally, the calibration pattern can also be provided on the inside wall of the housing and in the field of view of the image acquisition device. It is also possible to mark with a stamp seal, or provide a temporary tattoo on the skin surface of a patient and to use the area with the stamp or tattoo for calibrating the device before performing an acquisition.

Figure 3:
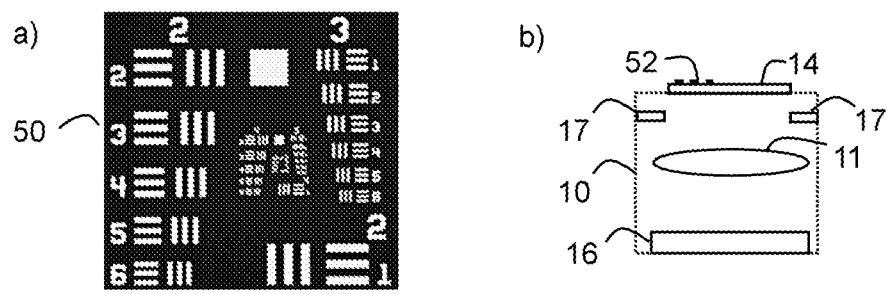
FIG. 3a) shows an example of calibration patterns and FIG. 3b) shows an embodiment of the present invention comprising a front glass with calibration pattern.

In one embodiment of the present invention, a calibration pattern can be provided directly onto the front glass. FIG. 3a) shows examples of calibration patterns. FIG. 3b) is the same as FIG. 2 with the addition of a pattern 52 on the lower surface of the front glass. The pattern 52 has been enlarged for clarity: these types of patterns are mostly manufactured by thin film deposition and the individual lines can have orders of magnitude down to the sub-micrometre.

The pattern 50 shown of FIG. 3a) has the advantage that it does not only provide information on the focus depth, but also information on the resolution by computing the modulation transfer function of the optical system with the pattern. However, the invention is not limited to such patterns. More simple patterns may also be used, such as simple lines or circles.

The calibration pattern can also be integrated within the front glass at an arbitrary depth from the front glass surface. If the distance to the image acquisition device, e.g. camera sensor (or lens, in case of using a moving image acquisition device, e.g. sensor) is known, the distance from the front glass surface can be compensated for. The pattern can in principle be positioned anywhere within the field of view of the camera, for example on the housing material itself provided its position gives is reproducible and provides reproducible focus depths when used for calibration.

The calibration process can be implemented by letting a camera autofocus arrangement obtain a sharp image of the pattern on the front glass (for example by implementing an edge detection method) at a given wavelength. Since the distance between the pattern and the image acquisition device, e.g. camera sensor is known, the corresponding digital driving level can be stored as a reference driving level of an absolute focus depth for the given wavelength.

The positions and distance from the calibration pattern to the front glass surface used as a reference viewing surface is important. The calibration procedure records the digital driving levels when the calibration pattern is sharp. This value can be extrapolated to find the relationship of digital driving levels to focus on depths deeper into the skin. This can be done from known characteristics of the device or by finding the calibration data with an external object having the required depth.

For image acquisition devices, e.g. cameras which are provided with a moving sensor together with a static lens, the distance between the lens and the sensor can be used. If the calibration pattern is placed on the lower surface of the front glass, and an object is placed in contact with the front glass as the viewing surface, the part of the object surface touching the front glass will be in focus when the reference driving level is used. If the device is calibrated for a given distance and a given wavelength, the reference driving level is known. The image acquisition procedure may start at all spectral bandwidths as the focal length can be extrapolated from one wavelength to all other wavelengths (or spectral bandwidths). Thus, images of the object at a plurality of depths may be acquired.

Figure 4:
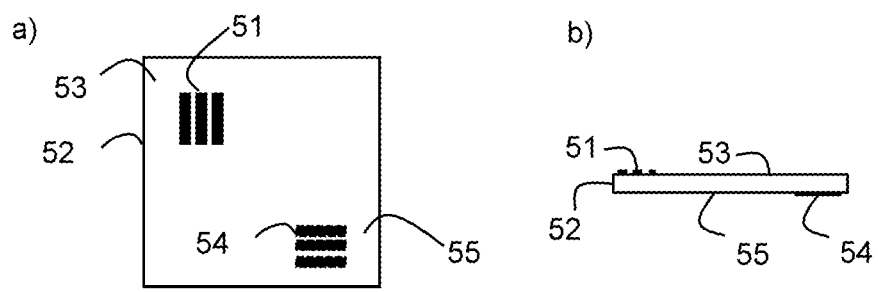
FIG. 4 shows an embodiment of the present invention comprising a front glass having two calibration patterns at a distance from each other.

In a second embodiment of the present invention, a second pattern is provided on or in the front glass as the reference viewing surface at a distance from the first pattern. For example, this can be implemented by providing the patterns on the upper and lower surfaces of the front glass, in which case they are separated by the thickness of the glass. FIG. 4 shows a) a top view and b) a side view of two patterns arranged at opposite sides of the front glass. A pattern 51 is provided on the upper surface of a front glass 52 on the front side 53. Another pattern 54 is put on the back side 55 of the front glass 52. By knowing the thickness of the glass it is possible to establish a relationship between the positions of the patterns 51 and 54 and the digital driving levels, assuming linearity of the system or a known/pre-defined/approximated non-linear behavior of the system. With this knowledge it is possible to steer the image acquisition device, e.g. camera to focus on a specific depth in the sample, and each image can be related to the absolute depth in the object where it was captured.

In principle, the patterns can be provided at an arbitrary distance to each other in the substrate. The distance to and within the skin is important. The distance to the static image acquisition device, e.g. camera or the static lens is an offset to this distance.

The patterns absolute positions in the substrate should at reproducible positions. The offset distances to the static image acquisition device, e.g. camera sensor or the static lens should be constant. It is preferred that the distance between them is larger than the depth of focus of the camera, in order for the image acquisition device, e.g. camera to differentiate between them. On the other hand thicker glass will result in geometric distortions. Thus, a preferred range of thickness for the front glass or substrate is about 0.8-1.4 mm, for example 1.1 mm, for a depth of focus of approximately 0.6 mm.

In the example shown on FIG. 11, the width of the tip of the device is in the range of 15 to 30 mm which can be too wide to access certain parts of the body for inspection, such as between fingers or toes. It can be beneficial to add a cone shaped extension piece with a narrower tip to the dermatoscope, to better match the shape of the body to be examined.

Figure 5:
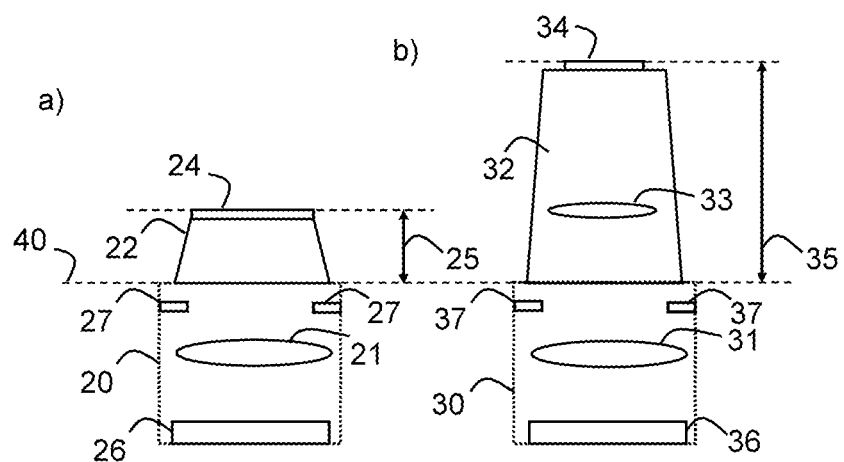
FIG. 5 shows an embodiment of the present invention comprising an extension piece.

FIG. 5 shows an embodiment of the present invention comprising extension pieces that can be put in front of the front glass of the dermatoscope. FIG. 5a) comprises the housing 20 an image acquisition device, e.g. camera having a camera lens 21, a camera sensor 26, a short cone 22 and a front glass 24. The cone 22 may be permanently integrated to the housing 20. If the length 25 of the extension piece 22 is moderate, the camera lens can be adapted to compensate for the additional length 25. However, for long extension pieces this might no longer be possible and an additional lens may be required. FIG. 5b) shows an example of a "longer" type of extension cone. It comprises the housing 30, an image acquisition device, e.g. a camera with a camera lens 31, a camera sensor 36, a long cone 32, a cone lens 33 and a front glass 34. The long cone 32 can be shaped so that it fits in more narrow angles of the body, such as for example between fingers or toes.

In embodiments where the regular cone can be removable and replaceable by an extension cone, then there would always be only one glass in front of the lens (as depicted in the current pictures). However, if the regular cone is not removable, then there will be an additional glass between the regular cone and the extension cone. The extension cone is basically added on top of the regular cone. This has the additional benefit of preventing dust or similar from getting into the device . . . .

Figure 6:
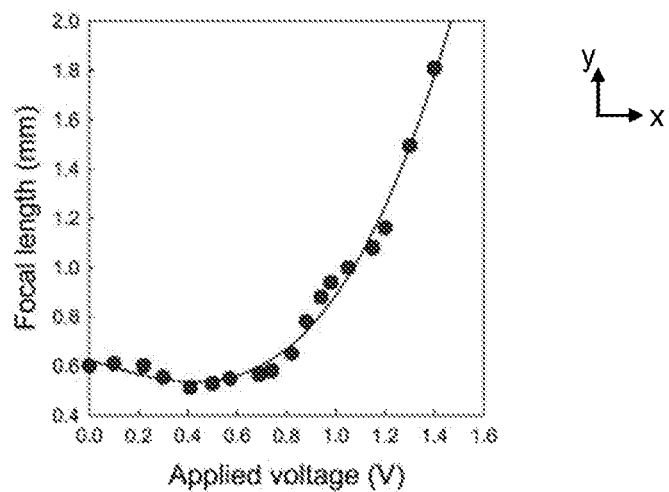
FIG. 6 shows the characteristics of a liquid lens.

If a non-linear type of focusing means is used, such as a camera lens, for example a liquid lens, this shift might force the focus to operate in a part of its range that is more difficult to manage, e.g. where a small change in voltage might yield a big change in focal length or where an increase in voltage reduces the focal length. The main goal of the present application is to operate in the part of the range for which the step size is smallest. FIG. 6 shows the relation between the focal length (on the y axis) and the applied voltage (on the x axis) for a liquid lens. For example, at focal lengths around 0.5-0.7 mm, small voltage steps will result in small changes in the focal length, which can make fine tuning easier. While for example at 1 mm, a small change in voltage yields a large step in focal length. However, in the lower part of the range 0.0 to 0.4 V, an increase in voltage results in a decrease in focal length. For some applications, it is desirable to keep the liquid lens operating at lower focal lengths, in an approximately linear part of the range. If an extension piece is used, it can be beneficial to insert a lens inside the piece, for example lens 33 in FIG. 3b), to reduce the focal length. The lens can be a conventional lens of simpler type than a liquid lens.

If an extension piece is used, the calibration pattern should be put at the front glass of the extension piece as the reference viewing surface.

Figure 7:
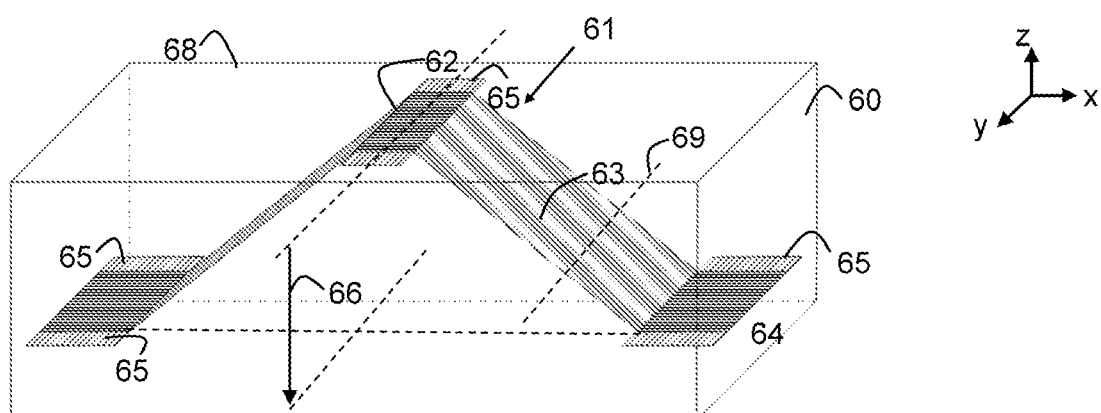
FIG. 7 shows an embodiment of the present invention comprising a three-dimensional calibration pattern.

In a third embodiment according to the present invention there is foreseen an additional three-dimensional calibration piece which is put in front of the front glass as reference viewing surface. The three-dimensional calibration piece can be any substrate, such as glass, plastic, etc. It can be transparent but this is not a requirement as it is removed when real measurements are performed. The pattern comprises a physical structure that is provided at a variety of known depths within the calibration piece (that can exceed the thickness of the front glass). A simple solution can for example be a substrate with straight parallel lines, which are in a plane which is tilted with respect to the plane of the image acquisition device, e.g. camera sensor. FIG. 7 illustrates an exemplary embodiment comprising a pattern 61 having parallel lines extending at different depths (z direction) of the substrate, the z direction corresponding to the optical axis of the device. The sample can be implemented by e.g. engraving such as laser engraving on a substrate, micro-lithography of a metal sheet, glass etching, milling, printing with ink, 3-dimensional printing or sub-surface laser engraving, but not limited thereto. The test pattern can be retrofitted and applied as a sticker on the cover glass of existing devices. The outer boundaries 60 can e.g. be the outer boundaries of a substrate. The substrate can be a stand-alone element, for example a metal sheet, where no surrounding material is necessary.

Assuming FIG. 7 comprises a substrate 60, a part 62 of the calibration pattern can extend horizontally (along the x-axis) in the surface 68, while other parts may be completely imbedded inside the substrate 60, for example the inclined horizontal lines 63 or the "flat" horizontal lines 64. Thus, the lines of the calibration pattern have a V shape with a flat and horizontal section in the vertex 62 and at the extremities 64. There can also be lines 65 in the vertical direction (along the y axis) which do not cross any of the horizontal lines 62, 63 or 64 in the flat sections. The pattern can be symmetric around the vertex 62.

The substrate or substrate with the three-dimensional pattern, e.g. engraved pattern can be attached or easily snapped or fixed by mechanical means for example to the front glass of the dermatoscope or an extension cone so that the upper surface 68 (or 62) of the substrate 60 is in contact with the lower surface of the front glass of the dermatoscope (or of the extension cone, in either case being the reference viewing surface) and the side 67 is facing outwards.

A reference level is considered to be at minimum level, e.g. 0 mm of depth. In FIG. 7 this reference plane coincides with the upper surface 68 of the substrate 60. The maximum level of depth of the pattern or structure 61 is indicated with arrow 65. The distance between the calibration lines of the pattern can be in the sub-mm range, for example 20-40 um. The lines can extend continuously across the substrate in the x-direction. The continuous lines make it possible to have a calibration pattern available for every driving level position of the camera focus for a given wavelength. First the camera can be made to focus with a given wavelength on a certain level, for example along the dashed line 69. The driving level is kept in memory and a relative focus function is calculated (based on for example edge detection) to give the horizontal position of the focus. In FIG. 7 the horizontal lines 63 can be described by a linear function z=kx+$x_0$ (initial), and by knowing the distance 66, the $x_0$ (initial) can be determined. And using the x value from the relative focus function, the depth can be calculated for the driving level in question. This procedure can be repeated for a multiple of different x values like 69. Note that due to the V shape of the three-dimensional calibration pattern, the measurements can be performed twice, and the average could be used as a result.

The pattern like the one in FIG. 7 may also further provide information on the resolution and MTF (Modulation Transfer Function) and the resolution of the camera system.

The substrate may also comprise numbers engraved inside wherein each number indicates the actual depth inside the substrate.

The calibration pattern can also include coloured elements so that the calibration pattern can be used for colour calibration. The calibration pattern may be a colour chart or a colour patch.

In another embodiment, instead of using a substrate, a phantom of human skin can be used to calibrate the sensor, e.g. a pig skin or an artificial piece of skin manufactured to be a phantom. Advantages are that such a phantom is more realistic and may improve the calibration. Such a phantom may only be used in the factory. As pig skin is very similar to human skin, a sample of pig skin may also be used as a calibration substrate for the device of the present invention. A 3D artificial skin tissue can be made as described in US 2016/0122723 which is incorporated herein by reference.

Figure 8:
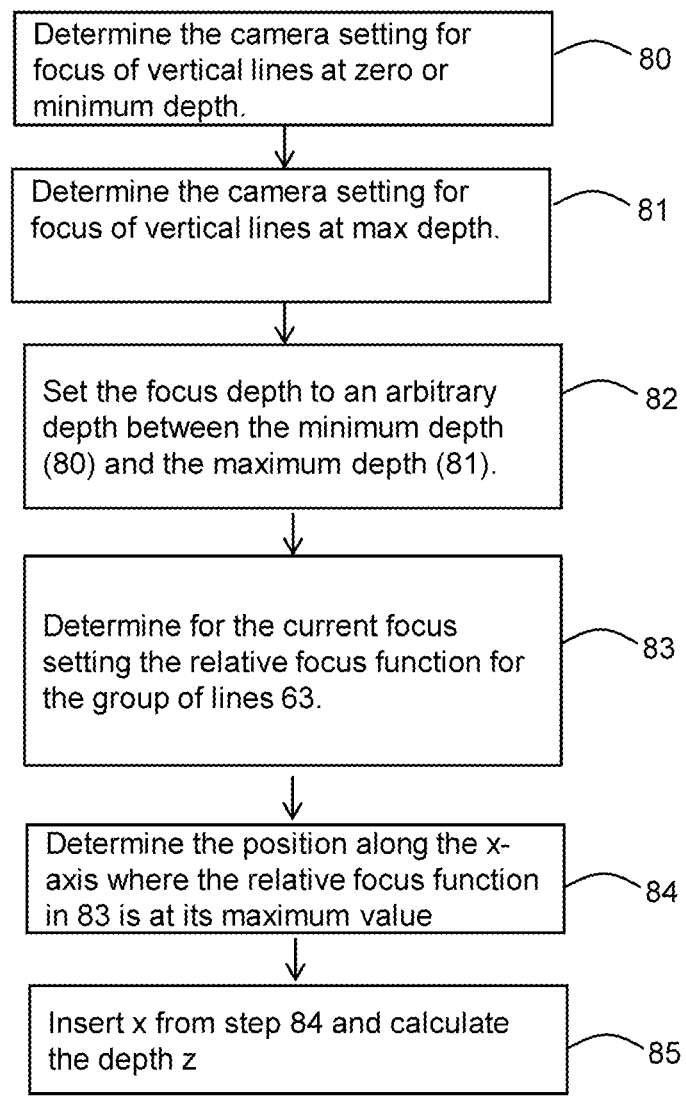
FIG. 8 shows a flow chart of an embodiment of the present invention.

FIG. 8 shows a flow chart describing an embodiment of the present invention where the image acquisition device, e.g. camera is calibrated using the structure in FIG. 7. In step 80, the image acquisition device, e.g. camera setting is determined when it is focused on the vertical lines 65 at 0 mm of depth, the reference level. In step 81, the image acquisition device, e.g. camera is being focused on the vertical lines 65 at a maximum depth, and the image acquisition device, e.g. camera settings are recorded. In step 82 the focus depth is set to an arbitrary depth between the minimum depth (80) and the maximum depth (81), in step 83, the current focus setting the relative focus function for the group of inclined lines 63 is determined. And in step 84, a focus function F(x) is calculated relative to the horizontal lines:

$$F(x) = \frac{\sum_y [f(y) \otimes i(x, y)]^2}{\sum_y [f_{center}]^2}$$

Where i(x, y) is the normalized image pixel value at location (x, y), f(y) is a one-dimensional high-pass filter kernel with center tap value $f_{center}$ and sum of the coefficients 0 (for example (−0.5, 1, −0.5)) and ⊗ is the convolution operator. In step 84, "Determine the position along the x-axis where the relative focus function in 83 is at its maximum value" and finally in step 85 performs the step: "Insert x from step 84 and calculate the depth z".

Figure 9:
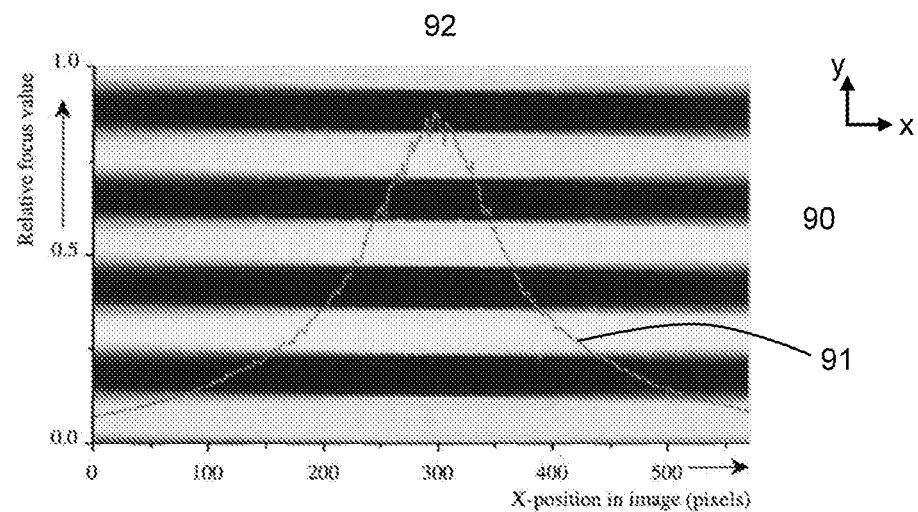
FIG. 9 shows an example of a relative focus function.

FIG. 9 shows an example of a relative focus function 91 overlaid onto a calibration pattern 90 (see Boddeke et. al., Journal of Microscopy vol. 186, Pt3 June 1997, pp 270-274).

The graph has the x-position on the x-axis and the relative focus value on the y-axis. The position of sharpest focus is considered to be at the top of the curve 92. This also corresponds to the visual appearance of the calibration pattern. The view of pattern 90 corresponds to looking straight onto the surface 68 in FIG. 8.

The present invention also provides the possibility of providing a temperature sensor in proximity of the liquid lens. As the driving voltage of the liquid lens, or the calibration of the liquid lens is dependent on temperature variations, such a temperature sensor can be used to compensate for variations in the focus as a function of temperature.

In one embodiment of the present invention, an additional pattern can used externally from the dermatoscope, for example in a charging station or docking station. A pattern can be for example lines for focus calibration (as described previously), but this could also be for example color patches with known color for color calibration.

Figure 10:
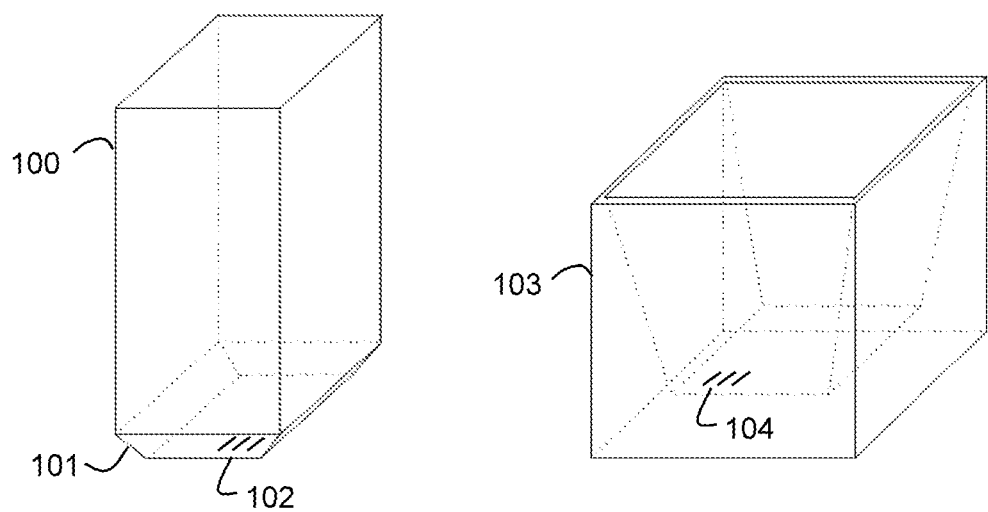
FIG. 10 shows an embodiment of the present invention comprising a calibration pattern on a charging station.

FIG. 10 shows a schematic illustration of a part of the dermatoscope 100, having a front glass 101 (as reference viewing surface) provided with a calibration pattern 102. The part 100 of the dermatoscope can be inserted into the charging station 103 so that a second calibration pattern 104 can be detected via the front glass 101 of the dermatoscope. The position of the part 100 of the dermatoscope when inserted inside the charging station 103 can be known so that the distance between the calibration patterns 102 and 104 can be used for calibration. In principle, the second pattern 104 can be positioned anywhere within the field of view of the camera of the dermatoscope.

One aspect of the present invention is to provide a dermatological inspection device. Such a device can be used to diagnose skin cancers such as melanomas.

Traditionally five signs have used by dermatologists to classify melanomas, "ABCDE" for Asymmetry, irregular Borders, more than one or uneven distribution of Color, a large Diameter (greater than 6 mm) and the Evolution of the moles.

In addition for nodular melanomas a different classification, EFG, is used which are Elevated: the lesion is raised above the surrounding skin.

Firm: the nodule is solid to the touch.

Growing: the nodule is increasing in size.

Thus, the elevation above the skin may also be used as means to detect and/or classify skin cancer lesions. It may also happen that such skin lesions are sunken under the skin level, as a cavity, for example in the case of melanoma ulceration.

In order to analyze the three-dimensional shape of skin lesions which may be cancer, a volume reconstruction algorithm based on shadows and reflection may be used.

A review of existing methods on Shape reconstruction from Shadows and Reflections: "Shape Reconstruction from Shadows and Reflections", Thesis by Silvio Savarese, 2005, California Institute of Technology. The following article by the same author also provides information on Shape Reconstruction, published in International Journal of Computer Vision, March 2007, Volume 71, Issue 3, pp 305-336, "3D Reconstruction by Shadow Carving: Theory and Practical Evaluation", by Silvio Savarese et. Al.

Different algorithms exist in order to reconstruct the shape of an object from its shadow. It is an object of the present invention to incorporate such a method into a dermatological inspection device. No restrictions are anticipated for the skilled person to find a suitable procedure to provide a 3D volume reconstruction based on shadows.

One of the first known algorithms proposed is called Shadow Carving. The algorithm uses the information of a cone by a point of observation and the silhouette in an image obtained from that point.

By using different viewpoints and intersecting the cones from these various viewpoints, the estimate of the object can be reconstructed. However, this method is not capable or reconstructing concavities in an object, which may be the case in the present invention.

Shafer and Kanade ("Using shadows in finding surface orientations", Computer Vision, Graphics, and Image Processing 22:145-176. 1983) established fundamental constraints that can be placed on the orientation of surfaces, based on the observation of the shadows one surface casts onto another. Embodiments of the present invention can use reconstruction methods where the light source positions are known. Also, reconstruction methods used image self-shadows, i.e. shadows cast by the object e.g. a skin lesion such as a melanoma upon itself and not shadows cast by other objects. A further assumption that can be made is that contour of the object, e.g. a skin lesion such as a melanoma, is defined by a smooth function and that the beginning and end of each shadow region can be found reliably. Each pair of points bounding a shadow region yields an estimate of the contour slope at the start of the shadow region, and the difference in height between the two points. For example, the information from shadows from images taken with a series of light sources at different positions can be used to obtain an interpolating spline that is consistent with all the observed data points.

Hence, in reconstructing a three-dimensional object from its shadows according to this embodiment of the present invention is to know precisely the position of the image acquisition device, e.g. imaging sensor, which is the viewpoint, and to know precisely the position of the light sources illuminating the object.

In order to be able to reconstruct the shape of a skin lesion with the device of the present invention, a plurality of light sources are added to the inspection device in addition to the first ring of light sources 1110. These additional light sources 1100 are arranged in a second ring so as to be in a proximity of the region of interest at the skin surface and so as to illuminate the region of interest. These light sources 1100 used for shadowing thus provide a horizontally directed illumination. These light sources are to be combined with the existing light sources 1110 which provide a more vertical illumination. Hence multiple light sources provide illumination of a surface skin lesion from perpendicular directions.

The inspection device according to these embodiments of the present invention further comprises a second ring of light sources 1100 provided near the front plate of the device according to the present invention in addition to the first ring of lights sources 1110. These light sources 1100 of the second ring provide a substantially horizontal illumination directed towards the region of interest at the surface of the skin, when said region of interest is in the middle of the ring of the tip of the device.

In a preferred embodiment according to the present invention, the ring 1100 of light sources provided in a proximity of the front plate comprises at least 4 light sources, more preferably 8 light sources and more preferably 16. As the tip of the inspection device is rectangular in an embodiment of the present invention, the light sources 1100 can be arranged in a rectangular ring in multiples of four. Knowing the exact position of each light source 1100, 1110 is advantageous to be able to reconstruct the three-dimensional shape of the object of interest.

As these light sources 1100 provide mostly a horizontal illumination, they are mainly used to cast shadows generated by protrusions extending above the skin surface. In an embodiment, these light source 1100 can be white LEDs.

Four light sources arranged in the second ring at 90° one from another surrounds the region of interest, however there is no redundant information. Ideally more light sources are provided to increase the number of shadows. A total of 8 or 16 light sources 1100 in the second ring in combination with seven or fourteen light sources 1110 in the first ring is a good compromise to provide enough information to be able to reconstruct the shape of the skin lesion. However, more light sources can also be used. Increasing the number of light sources increases the precision of the measurements but increases the processing time. Thus, in a preferred embodiment of the present invention, 12 to 25 light sources can be be used in the first and second rings providing horizontal and vertical illumination.

The image capturing device or sensor is located at approximately 70 mm from the front plate in the dermatoscope shown in FIG. 11.

If the object of interest such as a skin lesion comprises cavities, or concave regions, the light sources 1100 are capable of generating a shadow which corresponds to such a cavity but the cavity cannot be viewed. Therefore, the light sources 1110 of the first ring, which in an embodiment are color LEDs can be used. In the device according to an embodiment of the present invention, the first LED ring is located at 35 mm from the front plate. These will enable illuminating the skin lesion vertically and also the viewing of cavities in the region of interest and to assist in the reconstruction. In the example shown on FIG. 11, there are two arrays of seven LEDs, thus seven plus 16 or 23 total.

To generate sufficient images of shadows, the light sources 1110 and 1100 of the first and second rings are illuminated sequentially to generate images with the required shadows. The image acquiring device then acquires an image for each sequential illumination. For example, first the light sources of the second ring which are provided in proximity to the front surface are lit sequentially and then the light sources 1110 are lit sequentially providing illumination parallel to the optical axis.

Two light sources whose spectral bandwidth do not overlap or have a negligible overlap may acquire images simultaneously in order to reduce the acquisition time.

Given the large amount of images generated, which corresponds to the number of light sources, it is preferable to transfer the images acquired to a processor which has processing means to analyse the shadows of each image and reconstruct the three-dimensional shape of the object of interest.

To be able to penetrate the skin, high power LEDs are preferred. In order to achieve good image quality, it is necessary that each of the individual narrowband illuminations can be set to an output power which is sufficient (but also not too much) for the image acquisition device, e.g. sensor. With too low power, the noise will be very high for that spectral image, with too much power then there will be clipping and image quality will be bad as well. The present invention makes it possible to select the correct light output for each LED individually to match with the image acquisition device, e.g. sensor.

It is thus advantageous to be able to control the relative power of the individual narrow band illuminations independently. The setting of the relative power of the individual light sources depends on many factors such as the skin type of the patient, the specific lesion being imaged (red lesion, white lesion, . . . ) as well as the spectral characteristics of the image acquisition device, e.g. sensor.

Embodiments of the present invention provide means to modulate the power of the individual LED light sources relatively to each other, such that for a given (selected) gain/offset setting of the sensor, a good image quality can be achieved for all spectral images simultaneously. For example, it is possible to optimize the exposure, which can be the combination of exposure time (e.g. shutter speed), lens aperture and light intensity, for each light type. In doing so, a higher/optimal SNR and contrast can be obtained.

Also for polarized images the power of the polarized LEDs preferably is doubled (modulated) such that they can be combined with acquisitions of unpolarized light sources.

The aim of the device according to embodiments of the present invention is to acquire at each wavelength (thus seven times if there are seven types of light sources), a plurality of images, for example 5 to 10, each with a different depth into the skin in order to obtain information about the skin lesion at a plurality of depths, at each wavelength used. However, to acquire such a large number of images, thus 35 to 70 images, requires a lot of time. The number of frames per second is approximately 30. Thus, the acquisition of all the image data requires 1 to 2 seconds. A problem associated with long acquisition times is that a patient moves and thus the images suffer from motion artifact.

The imaging time can be decreased by acquiring several images, at the same depth of focus, with different spectral bands in parallel. For example: acquiring a red and blue image at the same time. This however requires to take into account the emission spectrum of the LEDs, and the filter spectrum of the image acquisition device, e.g. sensor to avoid crosstalk between the images taken simultaneously with different light sources. Hence, the images can be captured as long as there is no crosstalk (or predictable crosstalk which can be calculated).

Figure 15:
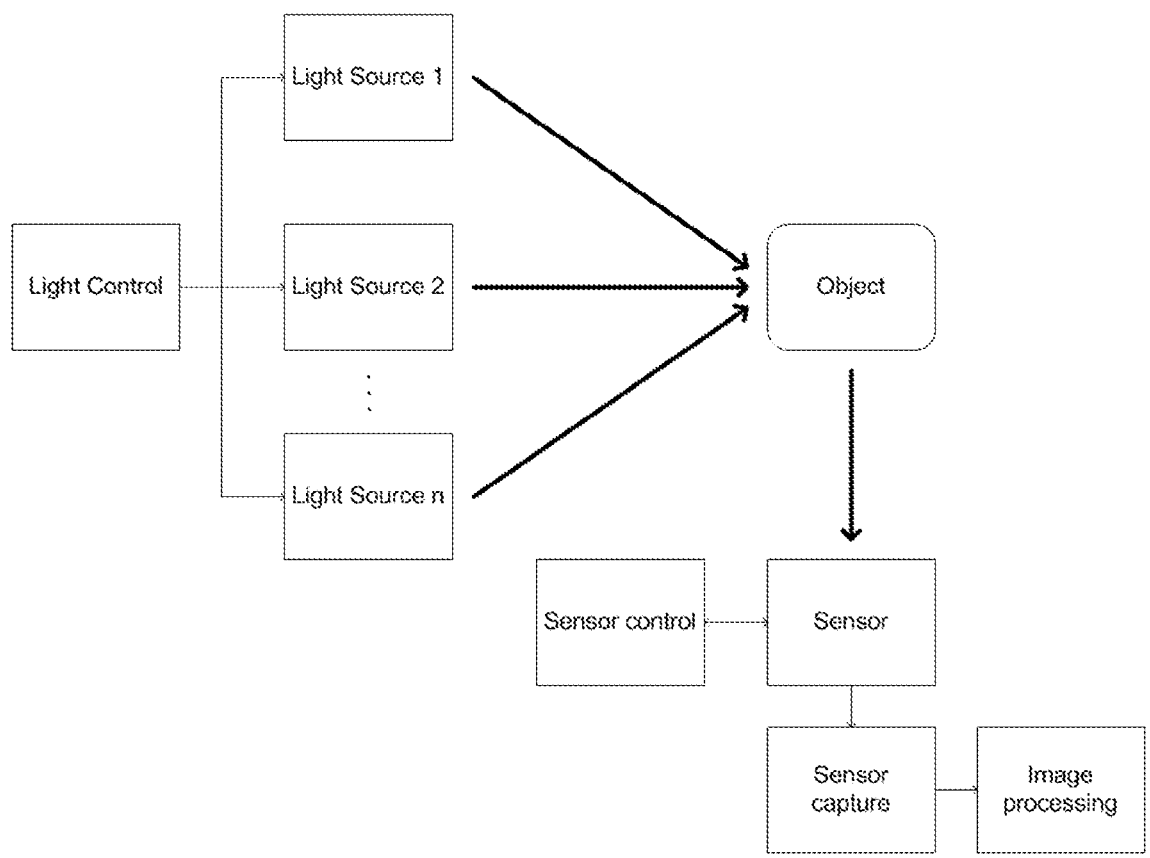
FIG. 15 shows a block diagram illustrating a method according to the present invention.

The image acquisition device, e.g. light sensor for these embodiments of the present invention can comprise a plurality of channels (see FIG. 15), each channel being configured to capture light in a different overlapping spectral bandwidth. As an example, consider a multi-channel sensor having the spectral sensitivity shown on FIG. 12 and $r(\lambda)$ represents the spectral sensitivity for the red channel or sub-pixel, $g(\lambda)$ represents the spectral sensitivity for the green channel or sub-pixel and $b(\lambda)$ the spectral sensitivity for the blue channel or sub-pixel.

The full spectral bandwidth of each light source is used when images are acquired. The small amount of noise/cross talk is removed by compensation. For example: The contribution of green sensor from the blue LED. The spectral power distribution of the light sources according to an embodiment of the present invention is shown on FIG. 13.

Figure 14:
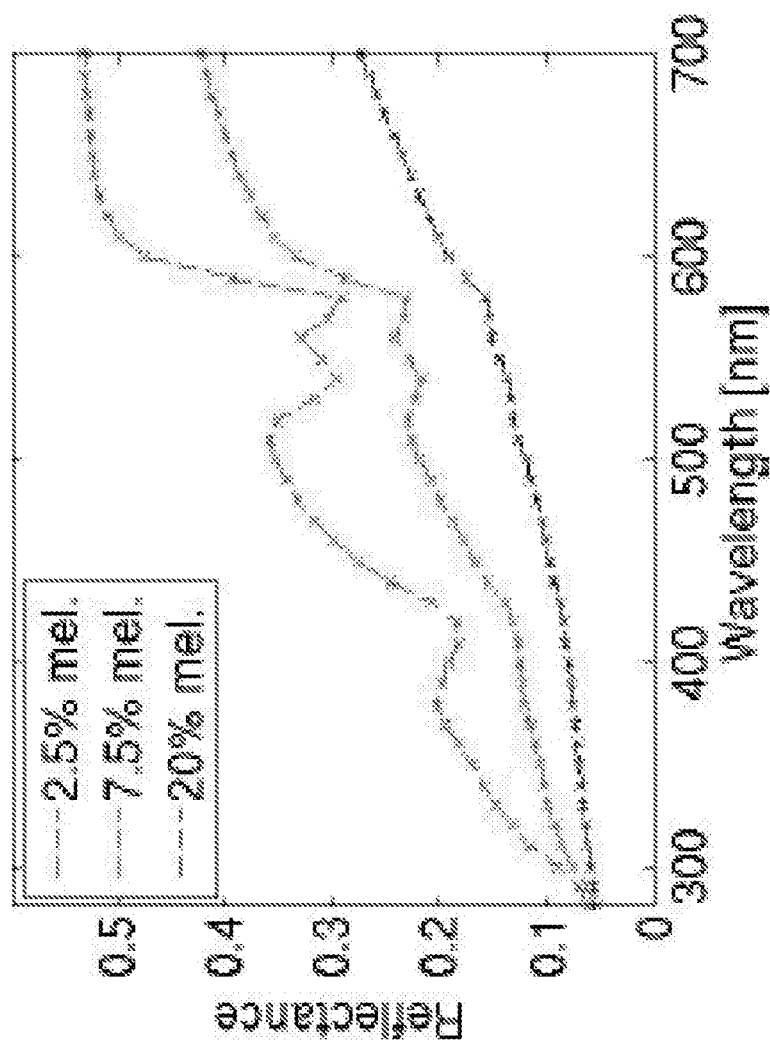
FIG. 14 the Skin reflectance in the wavelength regions of UVB (280-320 nm), UVA (320-400 nm) and visible (400-700 nm) for three different concentrations of melanosomes in the epidermis corresponding to skin types II, III and IV, respectively. This image is from "The optics of human skin: Aspects important for human health", by Kristian Pagh Nielsen, Lu Zhao, Jakob J Stamnes, Johan Moan in Solar Radiation and Human Health, Oslo: The Norwegian Academy of Science and Letters, 2008.

It is advantageous to take into account the type of skin which is being lit by the inspection device as the spectral bandwidth of the reflected object is different. For example, the skin can be skin with 7.5% melanomas in the epidermis, which corresponds to the middle curve of FIG. 14. The reflectance spectrum of the skin can be represented with a reflectance spectrum $R_{object}(\lambda)$, and is a function of the wavelength.

In order to explain this embodiment of the present invention, the contribution of each light source within each channel of the image acquisition device, e.g. sensor is calculated for a reference object having a reflectance spectrum $R_{object}(\lambda)$.

In a first step, one can calculate the output of the red, green and blue channels of the sensor when the reference object is illuminated with a first light source having a first spectral bandwidth BW1, for example a blue light source having a relative spectral power distribution $S_B(\lambda)$:

$$R_{Blue} = \int_{400}^{700} S_B(\lambda) * R_{object}(\lambda) * r(\lambda)$$

$$G_{Blue} = \int_{400}^{700} S_B(\lambda) * R_{object}(\lambda) * g(\lambda)$$

$$B_{Blue} = \int_{400}^{700} S_B(\lambda) * R_{object}(\lambda) * b(\lambda)$$

$R_{blue}$ represents output in the red channel of the sensor, and is calculated as the convolution between the spectral bandwidth associated to the red channel and the relative spectral power distribution $S_B(\lambda)$ of the light source convolved with a reflectance spectrum $R_{object}(\lambda)$ of a reference object. It represents the overlap between the relative power spectrum of the reflected illumination on the reference object and the spectral bandwidth of the red channel of the sensor.

Similarly, $G_{Blue}$ and $B_{Blue}$ represent respectively the output of the green and blue channel of the sensor when the reference object is illuminated with a blue light source.

Thus, when the power spectrum of the light source and the spectral bandwidth of the channel have the widest overlap, the output in that channel will be the greatest.

In this example, the output of the blue channel of the light sensor will be the greatest when the object of reference is illuminated with a blue light source.

Introducing the following ratios, which represent the ratio of blue light (from the blue light source) captured by each sub-pixel, or each channel, respectively the red, the green and the blue:

$$r_{Blue} = \frac{R_{Blue}}{R_{Blue} + G_{Blue} + B_{Blue}}, g_{Blue} = \frac{G_{Blue}}{R_{Blue} + G_{Blue} + B_{Blue}},$$

$$b_{Blue} = \frac{B_{Blue}}{R_{Blue} + G_{Blue} + B_{Blue}}$$

The ratio of blue light captured by the blue sub-pixels $b_{Blue}$ is the largest, for example 90%, as the overlap of the spectral bandwidth between the spectral sensitivity of the blue sub-pixel and the blue LED light spectrum is the largest. The ratio of blue light captured by the green sub-pixel a $g_{Blue}$ is thus the second largest, for example 8% and the ratio of blue light captured by the red sub-pixel, $r_{Blue}$, is thus the smallest for example only 2%.

Similarly, the output of each channel when a second light source having a second spectral bandwidth BW2, for example a red light source having relative spectral power distribution $S_R(\lambda)$ illuminates the same reference object, is provided by:

$$R_{Red} = \int_{400}^{700} S_R(\lambda) * R_{object}(\lambda) * r(\lambda)$$

$$G_{Red} = \int_{400}^{700} S_R(\lambda) * R_{object}(\lambda) * g(\lambda)$$

-continued $$B_{Red} = \int_{400}^{700} S_R(\lambda) * R_{object}(\lambda) * b(\lambda)$$

In this example, $G_{Red}$ represents the output of the green channel of the sensor when the object is illuminated with the red light source. Similarly, $B_{Red}$ represents the output of the blue channel when the object of reference is illuminated with a red light source.

Again, one can calculate the ratios expressing the amount of red light captured by each sub-pixel, or each channel:

$$r_{Red} = \frac{R_{Red}}{R_{Red} + G_{Red} + B_{Red}}, g_{Red} = \frac{G_{Red}}{R_{Red} + G_{Red} + B_{Red}},$$

$$b_{Red} = \frac{B_{Red}}{R_{Red} + G_{Red} + B_{Red}}$$

In this case, the ratio of red light $r_{Red}$ absorbed by red sub-pixels is assumed to be the largest, for example 92%, $g_{Red}$ the second largest, for example 7% and $b_{Red}$ the smallest ratio, for example only 1%.

It is now assumed that a different, but similar object (i.e. similar skin type), having reflectance spectrum $R'_{object}(\lambda)$, is simultaneously illuminated with the first and second light sources having first and second spectral bandwidth BW1 and BW2, in the example a red and blue light source, then the obtained red, green and blue sensor output are given by, assuming the system is linear:

$$R'_{Red+Blue} = \int_{400}^{700} S_R(\lambda) * R'_{object}(\lambda) * r(\lambda) + \int_{400}^{700} S_B(\lambda) * R'_{object}(\lambda) * r(\lambda)$$

$$G'_{Red+Blue} = \int_{400}^{700} S_R(\lambda) * R'_{object}(\lambda) * g(\lambda) + \int_{400}^{700} S_B(\lambda) * R'_{object}(\lambda) * g(\lambda)$$

$$B'_{Red+Blue} = \int_{400}^{700} S_R(\lambda) * R'_{object}(\lambda) * b(\lambda) + \int_{400}^{700} S_B(\lambda) * R'_{object}(\lambda) * b(\lambda)$$

This can be rewritten as:

$$R'_{Red+Blue} = r'_{Red+Blue} * (R'_{Red+Blue} + G'_{Red+Blue} + B'_{Red+Blue})$$

$$G'_{Red+Blue} = g'_{Red+Blue} * (R'_{Red+Blue} + G'_{Red+Blue} + B'_{Red+Blue})$$

$$B'_{Red+Blue} = b'_{Red+Blue} * (R'_{Red+Blue} + G'_{Red+Blue} + B'_{Red+Blue})$$

Each term can also be developed as:

$$R'_{Red+Blue} = \frac{r_{Red} + r_{Blue}}{r_{Red} + r_{Blue}} * r'_{Red+Blue} * (R'_{Red+Blue} + G'_{Red+Blue} + B'_{Red+Blue})$$

$$= \left( \frac{r_{Red}}{r_{Red} + r_{Blue}} * r'_{Red+Blue} + \frac{r_{Blue}}{r_{Red} + r_{Blue}} * r'_{Red+Blue} \right) *$$

$$(R'_{Red+Blue} + G'_{Red+Blue} + B'_{Red+Blue})$$

$$G'_{Red+Blue} = \left( \frac{g_{Red}}{g_{Red} + g_{Blue}} * g'_{Red+Blue} + \frac{g_{Blue}}{g_{Red} + g_{Blue}} * g'_{Red+Blue} \right) *$$

$$(R'_{Red+Blue} + G'_{Red+Blue} + B'_{Red+Blue})$$

-continued $$B'_{Red+Blue} = \left( \frac{b_{Red}}{b_{Red} + b_{Blue}} * b'_{Red+Blue} + \frac{b_{Blue}}{b_{Red} + b_{Blue}} * b'_{Red+Blue} \right) *$$

$$(R'_{Red+Blue} + G'_{Red+Blue} + B'_{Red+Blue})$$

The individual contribution of each light source type to each channel can now be estimated with the following relations, using the equations developed above:

$$R'_{Red} = \left( \frac{r_{Red}}{r_{Red} + r_{Blue}} * r'_{Red+Blue} \right) * (R'_{Red+Blue} + G'_{Red+Blue} + B'_{Red+Blue})$$

$$R'_{Blue} = \left( \frac{r_{Blue}}{r_{Red} + r_{Blue}} * r'_{Red+Blue} \right) * (R'_{Red+Blue} + G'_{Red+Blue} + B'_{Red+Blue})$$

$$G'_{Red} = \left( \frac{g_{Red}}{g_{Red} + g_{Blue}} * g'_{Red+Blue} \right) * (R'_{Red+Blue} + G'_{Red+Blue} + B'_{Red+Blue})$$

$$G'_{Blue} = \left( \frac{g_{Blue}}{g_{Red} + g_{Blue}} * g'_{Red+Blue} \right) * (R'_{Red+Blue} + G'_{Red+Blue} + B'_{Red+Blue})$$

$$B'_{Red} = \left( \frac{b_{Red}}{b_{Red} + b_{Blue}} * b'_{Red+Blue} \right) * (R'_{Red+Blue} + G'_{Red+Blue} + B'_{Red+Blue})$$

$$B'_{Blue} = \left( \frac{b_{Blue}}{b_{Red} + b_{Blue}} * b'_{Red+Blue} \right) * (R'_{Red+Blue} + G'_{Red+Blue} + B'_{Red+Blue})$$

wherein each individual term is known from a calibration performed with the reference object having reflectance spectrum $R_{object}(\lambda)$ and from measurements performed with the simultaneous illumination with the red and blue light sources.

Note that the accuracy of this technique is mainly determined by the similarity of the reflectance spectrum of the reference object and the measured object, i.e. of $R_{object}(\lambda)$ and $R'_{object}(\lambda)$ are. In the above example the object to be lit by multi-spectral light sources is assumed to be a certain skin type. If the actual skin type is very similar, then the obtained accuracy will be quite high.

If the object to be lit by the multi-spectral light sources is not known, then this technique could still be used by assuming a certain reflectance spectrum of the object, for example a flat spectrum.

As can be appreciated from the above the present invention provides a method for retrieving a first and a second spectral image of a multi-spectral image of an object illuminated simultaneously with a first and second light source of a dermatological inspection device, the spectral bandwidth of the light sources being comprised in the spectral sensitivity range of a light sensor. The method comprises the steps of Illuminating an object having a known reflectance spectrum $R'_{object}(\lambda)$ with the first and the second light source having a first BW1 and a second BW2 substantially distinct spectral bandwidths, Acquiring an image with the light sensor having a plurality of channels, each channel configured to capture light in a different overlapping spectral bandwidth, Retrieving each channel of the first and second spectral image from each channel of the acquired multi-spectral image and from a pre-calibrated ratio expressing the convolution between the spectral bandwidth associated to the channel and the first or second spectral bandwidth convolved with a reflectance spectrum $R_{object}(\lambda)$ of a reference object.

Each channel $C'_{j_{BW1}}$ and $C'_{j_{BW2}}$ of the first and second spectral image is obtained by calculating each channel j of the spectral image for the first and second spectral bandwidth $$C'_{j_{BW1}} = \left(\frac{c_{j_{BW1}}}{c_{j_{BW1}} + c_{j_{BW2}}} * c'_{j_{BW1+BW2}}\right) * \left(\sum_{i=1}^{n} C'_{i_{BW1+BW2}}\right)$$

$$C'_{j_{BW2}} = \left(\frac{c_{j_{BW2}}}{c_{j_{BW1}} + c_{j_{BW2}}} * c'_{j_{BW1+BW2}}\right) * \left(\sum_{i=1}^{n} C'_{i_{BW1+BW2}}\right)$$

wherein n is the number of channels of the light sensor, and $C_{j_{BW1}}$ is expressed by $$c_{j_{BW1}} = \frac{C_{j_{BW1}}}{\sum_{i=1}^{n} C_{i_{BW1}}}, c_{j_{BW2}} = \frac{C_{j_{BW2}}}{\sum_{i=1}^{n} C_{i_{BW2}}}$$

and wherein the outputs $C_{j_{BW1}}$ and $C_{j_{BW2}}$ of channel j when the reference object of reflectance spectrum $R_{object}(\lambda)$ is illuminated by a light source having spectral bandwidth BW1 and BW2, is expressed by $$C_{j\,BW1} = \int_{s1}^{s2} S_j(\lambda) * R_{object}(\lambda) * bw1(\lambda) \quad \text{and}$$
$$C_{j\,BW2} = \int_{s1}^{s2} S_j(\lambda) * R_{object}(\lambda) * bw2(\lambda)$$

wherein $S_j(\lambda)$ is the spectral sensitivity of channel j and $bw1(\lambda)$ and $bw2(\lambda)$ are the relative power spectrum of the first light source and second light source respectively, and s1 and s2 correspond to the lower and upper limits of the spectral sensitivity of the sensor.

The sensor can be an RGB sensor comprising three channels, e.g. respectively a red, a green and a blue channel.

In an embodiment of the present invention any of the methods described above suitable for use by an inspection unit can be implemented by a digital device with processing capability including one or more microprocessors, processors, microcontrollers, or central processing units (CPU) and/or a Graphics Processing Units (GPU) adapted to carry out the respective functions programmed with software, i.e. one or more computer programs. The software can be compiled to run on any of the microprocessors, processors, microcontrollers, or central processing units (CPU) and/or a Graphics Processing Units (GPU).

Such a device may be a standalone device such as a docking station or may be embedded in another electronic component, e.g. on a PCB board. The device may have memory (such as non-transitory computer readable medium, RAM and/or ROM), an operating system, optionally a display such as a fixed format display such as an OLED display, data entry devices such as a keyboard, a pointer device such as a "mouse", serial or parallel ports to communicate with other devices, network cards and connections to connect to a network.

The software can be embodied in a computer program product adapted to carry out the following functions when the software is loaded onto the respective device or devices or any other device such as a network device of which a server is one example and executed on one or more processing engines such as microprocessors, ASIC's, FPGA's etc.

The software can be embodied in a computer program product adapted to carry out the following functions, when the software is loaded onto the respective device or devices, and executed on one or more processing engines such as microprocessors, ASIC's, FPGA's, etc:
establishing a relationship between first adjustments of focusing means of the unit and the positions of the focus points along the optical axis of the unit, and storing a second adjustment wherein the focus position is at a fixed known position of a calibration pattern,
the step of storing a second adjustment comprising the step of analysing the calibration pattern at the known fixed position with an edge detection algorithm.

The software can be embodied in a computer program product adapted to carry out the following functions, when the software is loaded onto the respective device or devices, and executed on one or more processing engines such as microprocessors, ASIC's, FPGA's, etc:
Using a three-dimensional continuous calibration structure having a known extension in space which is placed at a known position with respect to the reference position,
instructing the image capturing device to establish an absolute reference value, engage a certain driving level relative the absolute reference value and use a focus function to obtain the coordinates corresponding to said driving level, using the calibration structure's extension in space to calculate the depth for the chosen driving level.

Any of the software mentioned above may be stored on a non-transitory signal storage means such as an optical disk (CD-ROM, DVD-ROM), magnetic tape, solid state memory such as a flash drive, magnetic disk such as a computer hard drive or similar.

While the invention has been described hereinabove with reference to specific embodiments, this was done to clarify and not to limit the invention. The skilled person will appreciate that various modifications and different combinations of disclosed features are possible without departing from the scope of the invention.

The invention claimed is:

1. A calibrated inspection unit for direct application to a skin surface of a patient, wherein a skin includes layers below the skin surface, said calibrated inspection unit comprising:
an optical array of elements in an optical path, said optical path comprising:
at least one light source,
an image capturing device configured to capture images and having a field of view,
a reference viewing surface through which the image capturing device is able to capture images,
an imaging lens having a radius of curvature and a focal length, wherein the imaging lens is configured to define a position of a focus point of the image capturing device that extends beyond the reference viewing surface along the optical path,
a fixed first calibration pattern located in a fixed position with respect to the reference viewing surface and located external to the reference viewing surface for contacting the skin surface, the fixed first calibration pattern being located at the fixed position that is at a depth that corresponds to at least one layer of the layers of the skin below the skin surface,
wherein the image capturing device is configured to capture an image of the fixed first calibration pattern, as a first image, and the image capturing device is configured to capture an image of the skin below the skin surface, as a second image, and
a focusing means for changing the focus position along the optical path as a function of adjustment values,
the calibrated inspection unit further comprising:
a calibration defining a relationship between the adjustment values of the focusing means and the positions of focus points below the skin surface, the adjustment values including a first adjustment value for the position of the focus point of the image capturing device at the fixed position of the fixed first calibration pattern, wherein the focusing means are provided by the imaging lens which is a liquid lens, and wherein the calibrated inspection unit is configured in a way such that the fixed first calibration pattern is configured to be used for focus calibration.

2. The calibrated inspection unit according to claim 1, wherein said at least one light source is centered on a first wavelength and has a first spectral bandwidth.

3. The calibrated inspection unit according to claim 2, further comprising a plurality of light sources, each light source being centered on a different wavelength and having a spectral bandwidth, and wherein first adjustment values of the focusing means and the positions of the focus points along the optical path are different for each wavelength or for different wavelengths.

4. The calibrated inspection unit according to claim 1, further comprising a second calibration pattern located in a second fixed position with respect to said reference viewing surface and in the field of view of the image capturing device, and a stored third adjustment value for a second focus position at the second fixed position of the second calibration pattern.

5. The calibrated inspection unit according to claim 1, further comprising a front plate in an exit pupil of the optical array, and wherein the fixed first calibration pattern is provided on at least one of the two surfaces of the front plate and/or inside the front plate.

6. The calibrated inspection unit according to claim 5, wherein a second front plate is provided at a second exit pupil and at least one further calibration pattern is provided on the second front plate.

7. The calibrated inspection unit according to claim 6, wherein the second optical array comprises a lens whose focal length relates to the length of the second optical array.

8. The calibrated inspection unit according to claim 1, wherein the focusing means is configured to be translated along an optical axis of the optical path or the focusing means is provided by the imaging lens which is the liquid lens.

9. The calibrated inspection unit according to claim 1, wherein the first and second adjustments values are driving voltages.

10. The calibrated inspection unit according to claim 1, wherein the fixed first calibration pattern is a three-dimensional pattern defining a plurality of fixed positions from the reference viewing surface wherein when said three-dimensional pattern is installable at an exit pupil, such that the focusing means further comprise a plurality of the adjustment values for a focus position at the plurality of fixed positions of the three-dimensional calibration pattern.

11. The calibrated inspection unit according to claim 1, wherein the fixed first calibration pattern comprises a pattern of lines which are in a plane which forms an angle with the plane of the image capturing device.

12. The calibrated inspection unit according to claim 11, wherein the fixed first calibration pattern comprises parallel of lines which are positioned in a plane parallel to the plane of the image capturing device.

13. The calibrated inspection unit according to claim 12, wherein distances between the parallel lines are correlated to their depth within a substrate.

14. The calibrated inspection unit according to claim 13, further providing a pre-determined potentially non-linear transformation for correcting a predefined or pre-calibrated relationship of a focus position along the optical path as a function of adjustment values.

15. The calibrated inspection unit according to claim 11, wherein the fixed first calibration pattern is a phantom of human skin.

16. The calibrated inspection unit according to claim 1, further configured to operate with a second optical array providing a second exit pupil.

17. The calibrated inspection unit according to claim 1, wherein calibration information is put in optical codes next to the fixed first calibration pattern.

18. The calibrated inspection unit according to claim 1, wherein the fixed first calibration pattern also comprises a color calibration.

19. The calibrated inspection unit according to claim 1, further comprising a means to detect when the viewing surface touches the skin.

20. The calibrated inspection unit according to claim 1, wherein the focusing means comprise an image processor configured for calculating a modulation transfer function of the optical array.

21. A method for calibrating an inspection unit for direct application to a skin surface of a patient, wherein a skin includes layers below the skin surface, said inspection unit comprising an optical array of elements comprising at least one light source having a first spectral bandwidth centred on a first wavelength, an image capturing device configured to capture images and having a field of view, a reference viewing surface through which the image capturing device is able to capture images, an imaging lens having a radius of curvature and a focal length, wherein the imaging lens is configured to define a position of a focus point of the image capturing device that extends beyond the reference viewing surface along an optical axis at said first wavelength, and a reference viewing surface, a focusing means for changing the focus position along the optical axis as a function of driving values, wherein the method comprises the steps of:

providing a fixed first calibration pattern located at a fixed position with respect to said reference viewing surface and located external to the reference viewing surface for contacting the skin surface and in the field of view of the image capturing device, the fixed first calibration pattern being located at the fixed position that is at a depth that corresponds to at least one layer of the layers of the skin below the skin surface, capturing by the image capturing device an image of the fixed first calibration pattern, as a first image, and capturing by the image capturing device an image of the skin below the skin surface, as a second image, establishing a relationship between adjustments of the focusing means and the positions of the focus points below the skin surface, the adjustments including a first adjustment value for the position of the focus point of the image capturing device at the fixed position of the fixed first calibration pattern, wherein the focusing means are provided by the imaging lens which is a liquid lens, and wherein the fixed first calibration pattern is configured to be used for focus calibration.

* * * * *